United States Patent [19]
Hawkins

[11] 3,983,142
[45] Sept. 28, 1976

[54] PEROXY COMPOUNDS AND PROCESSES FOR THEIR PREPARATION

[75] Inventor: Edwin George Edward Hawkins, Lower Kingswood, England

[73] Assignee: BP Chemicals International Limited, Great Britain

[22] Filed: Dec. 13, 1974

[21] Appl. No.: 532,587

Related U.S. Application Data

[62] Division of Ser. No. 651,969, July 10, 1967.

[30] Foreign Application Priority Data

| July 13, 1966 | United Kingdom | 31380/66 |
| Mar. 2, 1967 | United Kingdom | 9963/67 |
| Mar. 2, 1967 | United Kingdom | 9973/67 |
| May 20, 1967 | United Kingdom | 23546/67 |
| May 20, 1967 | United Kingdom | 23547/67 |

[52] U.S. Cl. ............ 260/348 C; 260/239.3 A; 260/307 F; 260/563 C; 260/563 R; 260/583 P; 260/584 R; 260/585 B; 260/610 R

[51] Int. Cl.² ............ C07D 303/04; C07C 179/08

[58] Field of Search ........ 260/563 R, 348 C, 563 C, 260/563 B

[56] References Cited
UNITED STATES PATENTS

3,206,510   9/1965   Weiss et al. .................. 260/563 C

OTHER PUBLICATIONS

Fremery et al. J. Org. Chem. 29 (1964) p. 2240.
Schulz et al. Angew. Chem. 77 (1965) p. 548.

*Primary Examiner*—Arthur P. Demers

[57] ABSTRACT

Peroxy compounds having the structural unit:

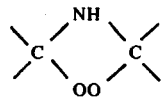

(I)

are useful for the production of monomers such as caprolactam which in turn may be polymerized to give useful polymers such as Nylon 6.

10 Claims, No Drawings

PEROXY COMPOUNDS AND PROCESSES FOR THEIR PREPARATION

This is a division of application Ser. No. 651,969 filed July 10, 1967.

The present invention relates to novel compounds containing a peroxy group.

These novel compounds may for example be used in the production of valuable monomers. For example;

A process for the production of derivatives of dodocan-1,12-dioic acid having nitrogen bound to the 12 carbon atom comprises heating 1,1'-peroxydicyclohexylamine

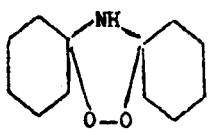

(Ia)

at elevated temperatures.

Examples of derivatives of dodecan-1,12-dioic acid containing nitrogen bound to the 12 carbon atom are

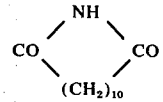

(IIa)

decan-1,10-dicarbonimide

HOOC-(CH$_2$)$_{10}$-CN     (IIIa)

11-cyano-undecanoic acid

HOOC(CH$_2$)$_{10}$-CONH$_2$     (IVa)

11-carbamoyl-undecanoic acid.

The starting material in the process, namely 1,1'-peroxydicyclohexylamine is a white solid insoluble in water but soluble in ethanol, which melts at 40° – 41.5°C and distills at 94° – 97°C at a pressure of 0.4 mm Hg and at 138°–140°C at a pressure of 12 mm Hg.

1,1'-Dihydroxydicyclohexyl peroxide

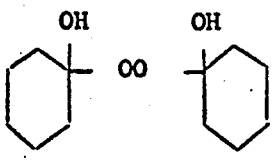

can be reacted with ammonia to give 1,1'-peroxydicyclohexylamine.

EXAMPLE A

To a stirred mixture of cyclohexanone (19.6 g) and ethanol (50 c.c.), kept at or below 0°C, was added 1-amino-3,3,5-trimethylcyclohexyl hydroperoxide (17.3 g, 78% pure); solution was complete in ca. 10 min. To the solution was added conc. sulphuric acid (3 drops) and magnesium sulphate and the mixture was stored at 0°C for 3 days. The solid was filtered off, the filtrate washed with water, dried and distilled, to give cyclohexanone, dihydroisophorone and a fraction (11.5 g), b.p. 90°–100° at 0.02 mm Hg, peroxide equivalent 179. By mass spectroscopy the product was shown to contain the unsymmetrical peroxide

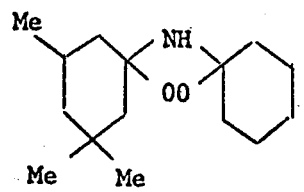

and the symmetrical peroxide 1,1'-peroxydicyclohexylamine in the ratio 1:9.

EXAMPLE B

Cyclohexanone (90 g), ammonia (50 c.c.) water (20 cc.), methanol (45 cc.) and E.D.T.A. (1 g) were stirred together and 30% hydrogen peroxide (70 cc.) gradually added with the reaction temperature kept at −35°. The mixture was stored at room temperature overnight, the product extract with ether, and the extract evaporated and the residue distilled to give cyclohexanone (22 g.) and a product which was identified as 1,1'-peroxy-dicyclohexylamine (64.4 g.), and leave a residue (2.0 g.). The peroxide distills at 94–97/0.4 mm, 138°–140°/12 mm, and has a melting point of 40°–41.5°.

EXAMPLE C

The same conditions were used as in Example B except that after the period of storage the bottom oily layer was separated, dissolved in ethanol, and the ethanolic solution added, with stirring, to water (2 liters). The 1,1'-peroxy-dicyclohexylamine separated as solid and filtered off. The yield of slightly wet product was 82 g., redistillation giving 72.6 g of pure peroxide.

EXAMPLE D

Cyclohexanone (90 g), 0.880 ammonia (32 cc.), water (20 cc.), methanol (45 cc.) and E.D.T.A. (0.2 g) were stirred together and 30% hydrogen peroxide (70 cc.) gradually added with the reaction temperature kept at −35°. The mixture was stored at room temperature overnight, the oily layer separated, diluted with an equal volume of methanol and the methanolic solution added, with stirring, to cold water (2 liters). Solid was filtered off and on distillation gave the peroxide 1,1'-peroxy-dicyclohexylamine (71.5 g).

EXAMPLE E

Cyclohexanone (90 g), 0.880 ammonia (50 cc.), water (20 cc.), methanol (45 cc.) and E.D.T.A. (1.0 g) were stirred together, and 30% hydrogen peroxide (70 cc.), added, with the reaction temperature kept at −35°. The temperature was kept at 35° for 4 hours and gaseous ammonia slowly passed into the solution. The mixture was stored overnight at room temperature; the peroxide crystallized out from the solution on addition of water and was filtered off. Distillation gave cyclohexanone (3.5 g) and 1,1'-peroxy-dicyclohexylamine (77.8 g). The aqueous phase was extracted with ether and provided cyclohexanone (4.8 g) and no peroxide.

EXAMPLE F 1,1'-Dihydroxydicyclohexyl peroxide (26.5 g), 0.880 ammonia (12.5 cc), water (35 cc.), methanol (12 cc.) and E.D.T.A. (0.2 g) were stirred together until the solid peroxide had dissolved and the mixture left at room temperature overnight. The product was extracted with ether and the ethered extract on distillation, gave cyclohexanone (<1 g) and 1,1'-peroxy-dicyclohexylamine (17.6 g).

The 1,1'-peroxydicyclohexylamine may also be made by reacting the autoxidate of cyclohexanol i.e. the product of oxidation of cyclohexanol with molecular oxygen, with ammonia.

EXAMPLE G 1-Aminocyclohexyl hydroperoxide (13.1 g), cyclohexanone (9.8 g), methanol (25 cc.) and ammonium acetate (1.0 g) were mixed and stored at 0° overnight. Next day the product was diluted with water, extracted with ether and the ethereal extract distilled to give unreacted cyclohexanone and 1,1'-peroxydicyclohexylamine (12.5 g), which recrystallized from petrol had m.p. 39.5°–40.5°, underpressed on admixture with authentic peroxide.

EXAMPLE H

1-Aminocyclohexyl hydroperoxide (13.1 g), dihydroisophorone (14 g), methanol (25 cc.) and ammonium acetate (1.0 g) were mixed, store at 0°C overnight and worked up as in the previous example. Distillation gave cyclohexanone and dihydroisophorone (9.0 g), an intermediate fraction (3.2 g), b.p. below 100°C/0.7 mm,Hg., a fraction (8.1 g), b.p. 110°–114°/0.7 mm of 3,3,5'-trimethyl-1,1'-peroxy-dicyclohexylamine (peroxide equivalent, 234; perchloric acid equivalent, 245; and residue (1.5 g). The process may be carried out in the liquid or gas phase, but is preferably carried out in the gas phase as the liquid phase reaction tends to give a complex mixture of products of which only part are the desired derivatives of 1,12-dodecanedioic acid. The elevated temperature to which the 1,1'-peroxydicyclohexylamine is heated is suitably in the range 300°C to 600°C, and preferably from 400°C to 600°C. If the reaction is to be carried out in the gas phase it is preferred to use reduced pressures. Suitable pressures are of the order of 10 to 250 mm Hg.

The vapour phase reaction may be carried out in any suitable manner, for example by feeding a solution of the peroxyamine into the top of a heated column, which may be packed with inert material e.g. glass balls and withdrawing the product containing the desired derivatives from the base. The pyrolysis is carried out in an atmosphere of an inert gas, e.g. nitrogen. Any solvent which is inert to the conditions of thermal pyrolysis may be used for dissolving the peroxide e.g. ethanol, pyridine, $\beta$-picoline, benzene, chloroform, aqueous ethanol, cyclohexanone, tributylamine, ethylene glycol. The solution may be of any desired concentration and suitably of 50% – 10% peroxide in solvent. The peroxide may also be fed as a vapour without solvent e.g. in a stream of inert gas.

The nature of the derivative of 1,12-dodecanedioic acid obtained by the process will depend on the conditions used. If the reaction is carried out in the vapor phase, the main products formed are decane-1,10-dicarbonimide (IIa), 11-cyano-undecanoic acid (IIIa), 11-carbomoyl-undecanoic acid (IVa). These three compounds are all white solids at room temperature, the imide (IIa) melting at 134° – 136°C., the nitrile-acid (IIIa) at 55° – 58°C and the acid-amide (IVc) at 132° – 134°C. The main products formed are the imide (IIa) and the nitrile-acid (IIIa) and the proportions in which these two compounds are found in the product are dependent on the temperature to which the starting material (Ia) is heated and the time for which it is maintained at that temperature. High temperatures and prolonged heating favour the formation of the nitrile-acid (IIIa) while the formation of the imide (IIa) is favoured by lower temperatures and shorter periods of heating. Thus, in the vapour phase reaction at 15 mm Hg at bath temperatures in the range 375° – 440°C the main constituent of the product was the imide (IIa) while at temperatures in the range 470° – 510°C the main constituent was the nitrile-acid (IIIa). At a given temperature the proportion of nitrile-acid is increased by increasing the pressure at which the thermal decomposition is carried out, by decreasing the rate of feed to the heated column or by increasing the concentration of peroxide in the solvent, i.e. by increasing the contact time.

The imide (IIa) and nitrile-acid (IIIa) may suitably be separated from the crude product obtained by heating the peroxyamine (Ia) in the vapour phase by dissolving the crude product in petrol, i.e. a light petroleum fraction boiling in the range 40° – 60°C and crystallizing the imide (IIa) or nitrile-acid (IIIa) by cooling or by distillation.

In addition to the $C_{12}$ compounds described above, the thermal decomposition of the 1,1'-peroxydicyclohexylamine yields smaller amounts of caprolactam and cyclohexanone, and other compounds.

The following examples in which all temperatures are in Celsius degrees and all pressures in millimeters of mercury illustrate the process.

EXAMPLE 1

The peroxide (Ia) (32 g.), dissolved in a mixture of ethanol (100 cc) and pyridine (4 cc), was fed dropwise during 3 hours into a 14 inch long glass tube half filled with glass balls and heated by a furnace to a temperature of 500° (at middle point). The pressure inside the reaction system was 150 mm and the pyrolysis was carried out in a slow stream of nitrogen. The product was condensed, the solvent removed and the residue distilled to give three fractions and a residue (0.9 g). The first fraction (2.8 g) was largely cyclohexanone but contained some pyridine; the second fraction (5.6 g) was mainly caprolactam; the third fraction (20.0 g) solidified and consisted mainly of 11-cyanoundecanoic acid (92.2% by titration).

EXAMPLE 2

The peroxide (Ia) (16 g) dissolved in $\beta$-picoline (25 g) was fed into the reactor used in Example 1 through which a slow stream of nitrogen was passed, at a temperature and pressure of 500° and 150 mm respectively during 115 minutes. Distillation provided cyclohexanone, a caprolactam fraction (3.1 g), a fraction (9.1 g) consisting largely of 11-cyanoundecanoic acid (88.5% by titration) and residue (0.7 g.).

EXAMPLE 3

The peroxide (Ia) (8g), dissolved in ethanol (40 cc) and pyridine (1 cc), was fed to the reactor used in Example 1 through which a slow stream of nitrogen was passed at a temperature and pressure of 590° and 15 mm respectively, during 60 minutes. Distillation gave a fraction (1.2 g) containing 50% caprolactam together with unreacted peroxide, and a fraction (5.0 g.) containing 87% 11-cyanoundecanoic acid together with caprolactam and imide (IIa), as well as residue (0.4 g).

EXAMPLE 4

The peroxide (I) (8 g) dissolved in ethanol (40 cc) and pyridine (1 cc) was fed to the reactor used in Example 1 through which a slow stream of nitrogen was passed at a temperature and pressure of 500° and 150 mm. respectively during 30 minutes. Distillation gave a caprolactam fraction (0.8 g), a fraction (5.7 g) containing 11-cyanoundecanoic acid (82% by titration) as well as caprolactam, and a residue (0.3 g.).

EXAMPLE 5

The peroxide (Ia) (8g) dissolved in ethanol (10 cc) and pyridine (1cc) was fed at a temperature and pressure of 500° and 150 mm respectively during 60 minutes into the reactor used in Example 1 through which a slow stream of nitrogen was passed. Distillation gave a caprolactam fraction (0.9 g), a fraction (5.4 g) containing 11-cyanoundecanoic acid (86 % by titration), and residue (0.3 g).

EXAMPLE 6

The peroxide (Ia) (8 g), dissolved in ethanol (40 cc) and pyridine (1 cc), was fed into the reactor used in Example 1 through which a slow stream of nitrogen was passed at a temperature and pressure of 400° and 150 mm respectively during 30 minutes. Distillation gave a caprolactam fraction (0.8 g), a fraction (5.5 g) containing 11-cyanoundecanoic acid (40% by titration) and imide (IIa) and a residue (0.4 g).

EXAMPLE 7

The peroxide (Ia) (10 g), dissolved in chloroform (20 cc) was fed to the reactor used in Example 1 through which a slow stream of nitrogen was passed at a temperature and pressure of 440° and 15 mm respectively during 35 minutes. Solvent was evaporated from the product, the residue treated with petrol, the solution cooled and imide (5.6 g) filtered off. The filtrate was evaporated and residue distilled to give cyclohexanone (0.7 g), a caprolactam fraction (0.9 g), and a fraction (1.6 g) containing mainly 11-cyanoundecanoic acid with some 11-carbamoylundecanoic acid (IVa).

EXAMPLE 8

Peroxide (Ia) (8 g) dissolved in pyridine (20 cc) and water (10 cc), was fed into the reactor used in Example 1 through which a slow stream of nitrogen was passed at a temperature and pressure of 510° and 15 mm respectively during 45 minutes. The product was dissolved in chloroform and dried with anhydrous magnesium sulphate. The solvent was evaporated and the residue mixed with petrol and cooled to yield 11-cyanoundecanoic acid (4.2 g). The filtrate was distilled to give a fraction (0.8 g), consisting mainly of caprolactam, and a fraction (1.0g), largely the nitrile-acid (IIIa).

EXAMPLE 9

Peroxide (Ia) (8 g) dissolved in cyclohexanone (20 g) was fed into the reactor used in Example 1 through which a slow stream of nitrogen was passed at a temperature and pressure of 440° and 15 mm respectively, during 40 minutes. The cyclohexanone was removed under reduced pressure and the residue treated with petrol and cooled to yield slightly impure imide (2.6 g). Distillation of the filtrate gave a caprolactam fraction (0.6 g) and a fraction (3.2 g), containing imide (IIa), cyanoundecanoic acid (IIIa) and carbamoylundecanoic acid (IVa).

EXAMPLE 10

Peroxide (Ia) (8 g) dissolved in a mixture of ethylene glycol (20 g) and ethanol (8 cc) was fed into the reactor used in Example 1 through which a slow stream of nitrogen was passed at a temperature and pressure of 440° and 15 mm. respectively during 40 minutes. The product was diluted with chloroform, washed with water to remove glycol and ethanol, the chloroform solution evaporated and petrol added to the residue. Cooling led to the separation of imide (4.0 g) and the filtrate was distilled to give cyclohexanone (0.7 g), a caprolactam fraction (0.5 g) and a fraction (1.3 g) containing the imide (IIa), nitrile-acid (IIIa) and amide-acid (IVa).

EXAMPLE 11

The imide (IIa) (3 g) dissolved in pyridine (10 cc) was fed into the reactor used in Example 1 through which a slow stream of nitrogen was passed at a temperature and pressure of 510° and 15 mm respectively during 45 minutes. From the product were isolated unreacted imide (1.6 g) and 11-cyanoundecanoic acid (1.1 g).

Caprolactam may be polymerized to give useful polymers viz nylon-6.

A process for the production of caprolactam comprises reacting 1,1'-peroxydicyclohexylamine with an alkali metal alkoxide.

1,1'-Peroxydicyclohexylamine is produced as hereinbefore described. 1,1'-Peroxydicyclohexylamine has the structure

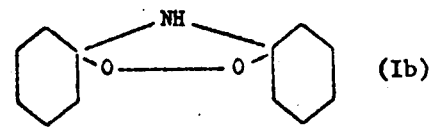

The alkali metal alkoxide may be an alkoxide of any of the alkali metals, e.g. lithium, sodium or potassium. Sodium is particularly preferred. The alkoxide is suitably a lower alkoxide e.g. ethoxide or methoxide, methoxides being preferred. The peroxyamine and the alkoxide may be reacted together in solution in a solvent such as aromatic hydrocarbons e.g. benzene, and alkanols e.g. ethanol or methanol. Solvents of high dielectric constant lead to high rates of reaction although the yield of caprolactam may be reduced. The preferred solvents are alkanols, preferably the alkanol corresponding to the alkoxide, thus when using a methoxide the reactants are preferably dissolved in methanol and when using an ethoxide the reactants are preferably dissolved in ethanol.

The ratio of the number of moles of alkoxide to the number of moles of 1,1'peroxydicyclohexylamine is suitably greater than 1:1. When the reaction is being carried out in solution the concentration of the reactants may vary within moderately wide limits.

The reaction is suitably carried out at moderately elevated temperatures. Thus temperatures up to 140°C may be used, preferably temperatures up to 100°C.

The duration of the reaction will vary with the temperature used, the reaction being complete with no more peroxide can be detected in the reaction mixture. The presence of unreacted peroxide may be detected by reacting the reaction mixture with a known quantity of potassium iodide in acetic acid. Any peroxide present liberates iodine which can be estimated by titration with sodium thiosulphate. Suitable times are in the range 0.5 to 10 hours.

The reaction can be carried out at sub-atmospheric and super-atmospheric pressure as well as at atmospheric pressure. The reaction may be carried out under conditions such that the solvent is able to reflux when heated sufficiently and the pressure may than be such that the solvent used to dissolve the reactants refluxes at the reaction temperature so helping to maintain the reaction temperature constant.

The caprolactam is recovered from the reaction mixture in any suitable manner for instance by diluting the reaction mixture with water followed by extraction of the mixture with a liquid which is immiscible with water and is a solvent for caprolactam. Suitable liquids are aromatic compounds, e.g. benzene, xylene, and chlorinated hydrocarbons, especially the chlorinated lower aliphatic hydrocarbons, e.g. methylene chloride, chloroform, dichloroethane. Ethers, e.g. diethyl ether may also be used. Acid may optionally be added to the reaction mixture after addition of water. The quantity of acid is suitably such as to make the reaction mixture just acid to Congo red indicator. The solvent used to dissolve the reactants may be removed before the dilution with water if desired. The liquid used to extract the caprolactam is then distilled from the extract to leave the caprolactam and cyclohexanone, which may be separated by e.g. distillation.

By using the process high yields of caprolactam and cyclohexanone are obtained, based on the equation:

and extracted with chloroform. Distillation gave cyclohexanone (4.1 g) and a caprolactam fraction (4.5 g), 87% pure by infra-red spectroscopy.

EXAMPLE 13

As in Example 11 but replacing methanol by ethanol. Heating time ½ hour. Distillation gave cyclohexanone (2.3 g), a caprolactam fraction (3.7 g), a higher boiling fraction (2.4 g) and residue (0.7 g). The caprolactam fraction contained 70% by weight of caprolactam by infra-red spectroscopy.

EXAMPLE 14

Sodium (1.2 g) was dissolved in ethanol (50 cc) and peroxide (Ib) (10 g) in ethanol (40 cc) added. The resulting solution was refluxed for 4 hours, the bulk of the ethanol removed on the water pump and the residue treated as in Example 11. There were obtained cyclohexanone (2.5 g), caprolactam fraction (4.0 g) containing 76% by weight of caprolactam, a higher-boiling fraction (1.2 g) containing 10 – 15% caprolactam, and a residue (0.5 g).

EXAMPLE 15

Potassium (3.4 g) dissolved in methanol (30 cc) was treated with the peroxide (Ib) (10 g) in methanol (10 cc) and the mixture refluxed for 2 hours. The reaction mixture was treated as in Example 11 and gave cyclohexanone (3.6 g), a caprolactam fraction (3.8 g) containing 83% caprolactam, by weight, and a residue (0.5 g).

EXAMPLE 16

Lithium (0.8 g) dissolved in methanol (40 cc) and

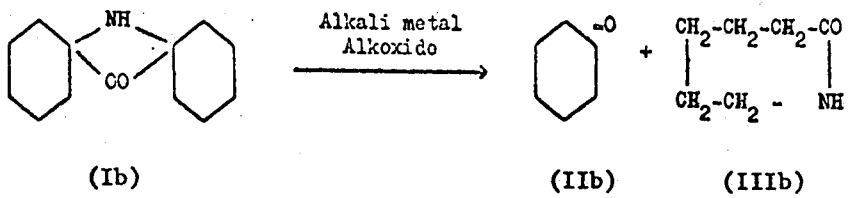

(Ib)  (IIb)  (IIIb)

The following Examples in which all temperatures are in celsius degrees and all pressures in millimeters of mercury illustrate this process.

EXAMPLE 11

Sodium (2g) was dissolved in methanol (30 cc) and the peroxide (Ib) (10 g), dissolved in methanol (10 cc), added. The mixture was heated under reflux for 1½ hours when no peroxide remained. Water (ca.30 cc) was added to the reaction mixture and the solution made just acid to Congo red with hydrochloric acid; extraction with chloroform followed by evaporation of the solvent and distillation at 15 mm. gave cyclohexanone (4.7 g) and a caprolactam fraction (4.2 g) containing 93% by weight of caprolactam (by infra-red spectroscopy).

EXAMPLE 12

As in Example 11 but at the end of the reflux period the bulk of the methanol was evaporated at 15 mm Hg, the residue diluted with water, neutralised with acid peroxide (Ib) (10 g) in methanol (10 cc were mixed and refluxed for 10½ hours. The reaction mixture was treated as in Example 1 and gave cyclohexanone (3.8 g), a caprolactam fraction, (2.7 g), containing 59% caprolactam by weight, a higher-boiling fraction (1.0 g) containing 30% caprolactam by weight, and residue (0.5 g).

EXAMPLE 17

Sodium (2 g) was dissolved in methanol (25 cc) and peroxide (Ib) (10 g) added, the mixture was refluxed for 1 hour. The reaction product was then diluted with water, and then extracted with chloroform without acidification to give cyclohexanone (2.9 g), a caprolactam fraction (4.8 g), containing 65% caprolactam by weight, a higher-boiling fraction (0.3 g), containing 37% caprolactam by weight and a residue (0.2 g).

Caprolactam may be polymerized to give useful polymers for instance nylon-6.

A process for the production of caprolactam comprises bringing 1,1'-peroxydicyclohexylamine into contact with an alkali metal hydroxide and an alkanol.

1,1'-Peroxydicyclohexylamine is produced as hereinbefore described. 1.1'-Peroxydicyclohexylamine has the structure

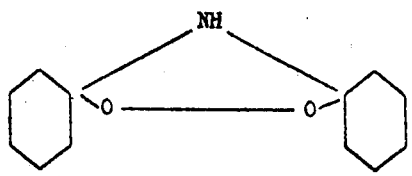

(Ib)

The alkali metal hydroxide may be a hydroxide of any of the alkali metals, e.g. lithium, sodium or potassium. Sodium hydroxide is particularly preferred.

Examples of suitable alkanols are the lower alkanols, e.g. methanol, ethanol and butanol. The quantity of alkanol used is preferably in excess of 1 mole of alkanol per mole of alkali metal hydroxide. Preferably the quantity of alkanol is such that both the alkali metal hydroxide and peroxyamine are dissolved. The peroxide and hydroxide are preferably brought into contact in the absence of added water, e.g. in solution in a substantially anhydrous alkanol. It may be advantageous to carry out the reaction in the presence of a drying agent e.g. CaO, MgSO$_4$.

The ratio of the number of moles of hydroxide to the number of moles of 1,1'peroxydicyclohexylamine is suitably greater than 1:1. When the reaction is being carried out in solution the concentration of the reactans may vary within moderately wide limits.

The reaction is suitably carried out at moderately elevated temperatures. Thus temperatures of 40° to 140°C may be used, preferably temperatures of 50° to 100°C.

The duration of the reaction will vary with the temperature used, the reaction being complete when no more peroxide can be detected in the reaction mixture. The presence of unreacted peroxide may be detected by reacting the reaction mixture with a known quantity of potassium iodide in acetic acid. Any peroxide present liberates iodine which can be estimated by titration with sodium thiosulphate. Suitable times are in the range 0.5 to 10 hours.

The reaction can be carried out at sub-atmospheric and super-atmospheric pressure as well as at atmospheric pressure. The reaction may be carried out under conditions such that the solvent is able to reflux when heated sufficiently and the pressure may then be such that the solvent used to dissolve the reactants refluxes at the reaction temperature so helping to maintain the reaction temperature constant. Cyclohexanone is produced a a by-product.

The caprolactam is recovered from the reaction mixture in any suitable manner for instance for diluting the reaction mixture with water followed by extraction of the mixture with a liquid which is immiscible with water and is a solvent for caprolactam. Suitable liquids are aromatic compounds e.g. benzene, xylene, and chlorinated hydrocarbons, especially the chlorinated lower aliphatic hydrocarbons, e.g. methylene chloride, chloroform, dichloroethane. Ethers, e.g. diethyl ether may also be used. Acid may optionally be added to the reaction mixture after addition of water. The quantity of acid is suitably such as to make the reaction mixture just acid Congo red indicator. The solvent used to dissolve the reactants may be removed before the dilution with water if desired. The liquid used to extract the caprolactam is then distilled from the extract to leave the caprolactam and cyclohexanone, which may be separated by e.g. distillation.

By using the process high yields of caprolactam and cyclohexanone are obtained, based on the equation:

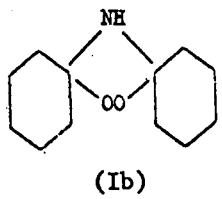
(IIb)

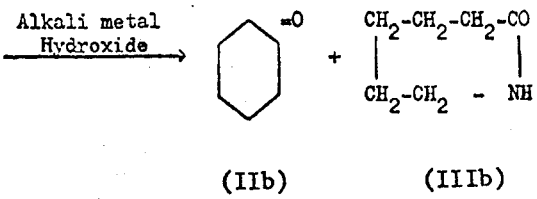
(IIIb)

The following Examples in which all temperatures are in celcius degrees and all pressures in millimeters of mercury illustrate the process.

EXAMPLE 18

Sodium hydroxide (3.5 g) was heated with methanol (30 cc) and peroxide (10 g) dissolved in methanol (10 cc) was added and the mixture heated to reflux for 2½ hours. After heating the solution was diluted with water and extracted with chloroform. Distillation gave a cyclohexanone fraction (4.0 g), a caprolactam fraction (4.4 g) (containing 75% lactam by I.R.), and residue (0.1 g.).

EXAMPLE 19

The same reactants were used as in Example 18 with the addition of magnesium sulphate monohydrate (1.5 g) to the refluxing solution. Heating was continued for 5¼ hours. Treatment of the reaction mixture as in Example 18 gave a cyclohexanone fraction (2.8 g), a caprolactam fraction (4.1 g containing 81% lactam by I.R.), and residue (0.2 g). Further caprolactam (0.2 g) was obtained by acidification of the aqueous phase followed by extraction with chloroform.

EXAMPLE 20

The same reactants were used as in Example 18 with the addition of calcium oxide (2 g) to the refluxing solution. Heating was continued for 2¼ hours. Treatment of the reaction mixture as in Example 18 gave a cyclohexanone fraction (3.7 g), a caprolactam fraction (4.2 g; containing 85% lactam by I.R.) and residue (0.2 g).

EXAMPLE 21

The same reactants were used as in Example 18 with the addition of water (2 cc) to the refluxing solution. Heating was continued for 3 hours. Treatment of the reaction mixture as in Example 18 gave a cyclohexanone fraction (3.3 g), a caprolactam fraction (4.5 g; containing 65% lactam by I.R.) and residue (0.2 g).

EXAMPLE 22

Potassium hydroxide (4.9 g), methanol (40 cc) and peroxide (10 g) were heated together under reflux for 2¾ hours. Treatment of the reaction mixture as in Example 18 gave a cyclohexanone fraction (1.9 g), a caprolactam fraction (4.4 g; containing 80% lactam by I.R.), and a higher-boiling fraction (0.4 g; containing 55% lactam by I.R.).

EXAMPLE 23

Sodium hydroxide (3.5 g), ethanol (70 cc) and peroxide (10 g) were heated under reflux for 2¾ hours. Treatment of the reaction mixture as in Example 18 gave a low-boiling fraction (1.7 g), a caprolactam fraction (4.2 g; containing 75% lactam by I.R.) a higher-boiling fraction (0.9 g) and residue (0.4 g).

EXAMPLE 24

Sodium hydroxide (3.5 g), ethanol (40 cc) and peroxide (10 g) were heated under reflux for 1¾ hours. Treatment of the reaction mixture as in Example 18 gave a low-boiling fraction (3.2 g; largely cyclohexanol by I.R.), a caprolactam fraction (3.9 g; containing 60% lactam by I.R., a higher-boiling fraction (1.2 g) and residue (0.5 g).

A process for the production of derivatives of dodecane-1,12-dioic acid having nitrogen bound to the 12 carbon atom comprises photo-chemically decomposing 1,1'-peroxydicyclohexylamine

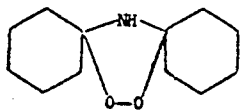
(Ia)

Examples of derivatives of dodecane-1,12-dioic acid containing nitrogen bound to the 12 carbon atom are

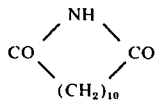
(IIa)

decane-1,10-dicarbonimide

HOOC-(CH$_2$)$_{10}$-CN    (IIIa)

11-cyano-undecanoic acid

HOOC (CH$_2$)$_{10}$-CONH$_2$    (IV a)

11-carbamoyl-undecanoic acid

The starting material in the process, namely 1,1'-peroxydicyclohexylamine is produced as hereinbefore discussed.

The compound (Ia) is photo-chemically decomposed by any of the known techniques of photo-chemical decomposition. The photo-chemical decomposition may be carried out by using ultra-violet light to irradiate the starting material (Ia).

Examples of suitable wavelengths of ultra-violet light which may be used are those in the range 3,600 A to 1,850 A, for instance those in the range 3,600 A to 3,100 A. An example of a suitable source of ultra-violet light is the mercury vapour discharge lamp, which may have for example a quartz envelope to allow shorter wavelengths to be transmitted than is possible with glass envelopes. Other glasses, for instance borosilicate glasses may, however, be used successfully instead of quartz.

The temperature and pressure at which the reaction is carried out are not critical. Thus temperatures in the range −50° to 50°C may be used but it is convenient to use temperatures close to ambient temperature, e.g. 10° − 30°C, and atmospheric pressures. It may be advantageous to provide for cooling of the reaction mixture which is being photo-chemically decomposed. This may be done by e.g. circulating cooling fluid between the the source of the radiation and the reaction mixture. The reaction is preferably carried out in the liquid phase and this may be done by dissolving the starting material (Ia) in a solvent. Examples of suitable solvents are ethanol pyridine, β-picoline, benzene, chloroform, cyclohexanone, tributylamine, ethylene glycol. The concentration of the peroxide (Ia) in the solvent may vary within moderately wide limits. Examples of suitable concentrations are those in the range 2 to 24% wt/volume (i.e. wt. of solute against volume of solvent). Suitable concentrations within the above range are for instance those between 8 and 24% wt./volume. It may be advantageous to add an initiator to the starting material (Ia) to assist the photo-chemical decomposition.

The principal product of the process is the imide (IIa), but the nitrile acid (IIIa) and amide (IIa) may also be obtained, though generally in smaller quantities. Cyclohexanone and caprolactam are also produced in the process of the present invention and may be recovered.

The imide (IIa) may be recovered from the reaction product by any suitable means for instance by dissolving the crude product in 40° − 60°C petrol (a light petroleum distillate substantially free of aromatics and boiling in the range 40° − 60°C at atmospheric pressure), and crystallizing the imide (IIa) from the solution in petrol.

The process is furher illustrated by the following examples.

EXAMPLE 25

The apparatus used consisted of a tubular U.V. source, consisting of a mercury vapour discharge lamp surrounded by two concentric tubes of borosilicate glass. The tube next adjacent to the lamp carried a stream of water, which cooled a solution of 1,1'-peroxydicyclohexylamine (Ia) (5g) in benzene (130 cc), located in the space between the tube next adjacent to the lamp and the tube next outwards from the lamp. The solution of the starting material (Ia) was kept mixed by a stream of nitrogen bubbles fed into the solution from a sintered glass disc sealed into the base of the tube surrounding the reaction mixture.

The solution of the starting material (Ia) was irradiated by the lamp for 10 hours and the solvent was then removed by evaporation under reduced pressure. The residue was mixed with 40° − 60°C petrol (i.e. light petroleum distillate substantially free of aromatics and boiling in the range 40° to 60°C at atmospheric pressure) to precipitate the imide (IIa).

The imide precipitated as above was filtered off and re-crystallized from ethanol and the filtrate remaining after removal of the precipitate was separated by distillation into fractions. The products obtained were (a) 1.3 g. of solid imide (IIa) (m.p. 132°−134°C) (b) 0.8 g. of a fraction boiling in the range 120° − 160°C at 14 mm Hg, and containing 30% by wt. caprolactam, (c) 0.8 g. of a fraction boiling in the range 160° – 230°C and 14 mm Hg and containing 15% by wt. caprolactam together with quantites of imide (IIa) and (d) 0.4 g. of residue.

EXAMPLE 26

The same reactants and conditions were used as in Example 25 except that 15 g. of peroxide (Ia) were used and iradiation with the lamp was continued for 22 hours. The products obtained were (a) 4.2 g. of solid imide (IIa), (b) 0.7 g. of a distillate fraction consisting of cyclohexanone, (c) 1.7 g. of a fraction boiling in the range 135° – 160°C at 15 mm Hg and containing 90% by wt. of caprolactam, (d) 4.4 g. of a fraction boiling in the range 160° – 235°C at 15 mm Hg and containing about 20% by wt. of caprolactam together with other amides, (e) 1.4 g. of a fraction boiling in the range 238° – 285°C at 15 mm Hg and containing imide (IIa) and (f) 0.9 g. of residue.

EXAMPLE 27

The same reactants and conditions as in Example 26 were used except that benzophenone (1.0 g.) was present with the peroxide (Ia) and the solution was irradiated for 24 hours. The products obtained were (a) 3.7 g. of solid imide (IIa), (b) 0.6 g. of cyclohexanone distillate fraction (c) 1.6 g. of a fraction boiling in the range 100°C to 180°C at 14 mm Hg, containing 55% by weight of caprolactam, (d) 4.4 g. of a fraction boiling in the range 180° – 290°C at 14 mm Hg containing secondary amides, (e) and 2.1 g. of residue.

EXAMPLE 28

The same conditions were used as in Example 27 but 2-methylanthraquinone (0.2 g.) was used in place of benzophenone, and irradiation with the lamp was carried out for 25½ hours. The products obtained were (a) 4.3 g. of the solid imide (IIa), (b) 0.3 g. of cyclohexanone, (c) 1.8 g. of a fraction boiling in the range 130° – 170°C at 15 mm Hg containing 48% by wt. of caprolactam, (d) 4.5 g. of a fraction boiling in the range 170° to 270°C at 15 mm Hg, (e) and 1.6 g. of residue.

EXAMPLE 29

The same conditions were used as in Example 26 except that the benzene was replaced by ethanol (125 cc) and irradiation with the lamp was carried out for 19 hours. The products obtained were (a) 4.0 g. of solid imide (II), (b) 0.6 g. of cyclohexanone, (c) 3.2 g. of a fraction boiling in the range 135 to 160°C at 15 mm Hg and containing 40% by wt. of caprolactam, (d) 3.9 g. of a fraction boiling in the range 160° – 245° at 15 mm Hg, containing amides, and (e) 1.3 g. of residue.

EXAMPLE 30

The same conditions as Example 26 were used except that the benzene was replaced by pyridine (125 cc) and irradiation with the lamp was carried out for 29 hours. The products were (a) 4.0 g. of solid imide (IIa), (b) 0.7 g. of cyclohexanone, (c) 3.5 g. of a fraction boiling in the range 130° to 170°C at 15 mm Hg, containing caprolactam, (d) 3.5 g. of a fraction boiling in the range 170° to 245°C at 15 mm Hg containing a linear secondary amide and 1.3 g. of residue.

Caprolactam may be polymerized to give useful polymers viz. nylon-6.

A process for the production of caprolactam comprises reacting 1,1'-peroxydicyclohexylamine with an alkali metal alkoxide or aroxide.

1,1'-Peroxydicyclohexylamine is produced as hereinbefore described. 1,1'-Peroxydicyclohexylamine has the structure:

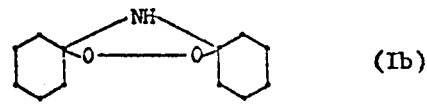

The term "aroxides" as used herein means compounds formed by the replacement of hydrogen by a metal in a hydroxy group linked directly to an aromatic nucleus. An example of a suitable aroxide is sodium phenoxide

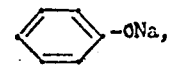

but other phenoxides including phenoxides with substituents other than hydroxy groups may be used. Aroxides derived from compounds having more than one hydroxy group linked to the aromatic nucleus may be used. The preferred aroxides are those derived from the benzene nucleus.

The alkali metal alkoxide or aroxide may be an alkoxide or aroxide of any of the alkali metals, e.g. lithium, sodium or potassium. Sodium is particularly preferred. Examples of suitable alkoxides are the lower alkoxide, e.g. ethoxide or methoxide, methoxides being preferred. Butoxides, in particular n-butoxides are suitable and the use of n-butoxides is particularly advantageous, as they can be isolated from the reaction of n-butanol and alkali metal hydroxides. The peroxyamine and the alkoxide or aroxide may be reacted together in solution in a solvent such as aromatic hydrocarbons, e.g. benzene, phenols and alkanols, e.g. ethanol or methanol. Solvents of high dielectric constant lead to high rates of reaction although the yield of caprolactam may be reduced. The preferred solvents are alkanols and when an alkoxide is used, the alkanol is preferably the alkanol corresponding to the alkoxide, thus when using a methoxide the reactants are preferably dissolved in methanol and when using an ethoxide the reactants are preferably dissolved in ethanol. However, when using higher alkoxides and aroxides the lower alkanols are the most suitable solvents. Thus, when using an n-butoxide, or a phenoxide, the most satisfactory results are obtained if the reaction with 1,1'peroxydicyclohexylamine is carried out in methanol.

Examples of suitable ratios of the number of moles of alkoxide or aroxide to the number of moles of 1,1'peroxydicyclohexylamine are those greater than 1:1. When the reaction is being carried out in solution the concentration of the reactants may vary within moderately wide limits.

The reaction is suitably carried out at moderately elevated temperatures. Thus, temperatures of 40° to 140°C may be used, preferably temperatures of 50° to 100°C.

The duration of the reaction will vary with the temperature used, the reaction being complete when no more peroxide can be detected in the reaction mixture. The presence of unreacted peroxide may be detected by reacting the reaction mixture with a known quantity of potassium iodide in acetic acid. Any peroxide present liberates iodine which can be estimated by titration with sodium thiosulphate. Suitable times are in the range 0.5 to 10 hours.

The reaction can be carried out at sub-atmospheric and super-atmospheric pressure as well as at atmospheric pressure. The reaction may be carried out under conditions such that the solvent is able to reflux when heated sufficiently and the pressure may then be such that the solvent used to dissolve the reactants refluxes at the reaction temperature so helping to maintain the reaction temperature constant.

The caprolactam is recovered from the reaction mixture in any suitable manner for instance by diluting the reaction mixture with water followed by extraction of the mixture with a liquid which is immiscible with water and is a solvent for caprolactam. Examples of suitable liquids are aromatic compounds, e.g. benzene, xylene, and chlorinated hydrocarbons, especially the chlorinated lower aliphatic hydrocarbons, e.g. methylene chloride, chloroform, dichloroethane. Ethers, e.g. diethyl ether may also be used. Acid may optionally be added to the reaction mixture after addition of water. The quantity of acid is suitably such as to make the reaction mixture just acid to Congo red indicator. The solvent used to dissolve the reactants may be removed before the dilution with water if desired. The liquid used to extract the caprolactam is then distilled from the extract to leave the caprolactam and cyclohexanone, which may be separated by e.g. distillation.

By using the process high yields of caprolactam and cyclohexanone are obtained, based on the equation:

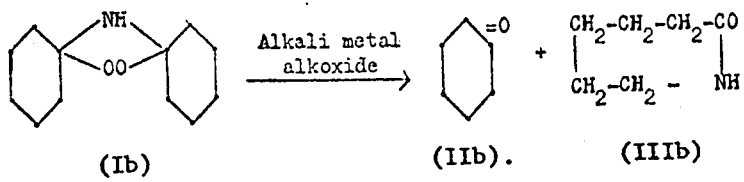

The process will now be illustrated by the following Examples in which all temperatures are in celsius degrees and all pressures in millimeters of mercury.

EXAMPLE 31

Sodium (2g) was dissolved in methanol (30 cc) and the peroxide (Ib) (10 g), dissolved in methanol (10 cc), added. The mixture was heated under reflux for 1½ hours when no peroxide remained. Water (ca. 30 cc) was added to the reaction mixture and the solution made just acid to Congo red with hydrochloric acid; extraction with chloroform followed by evaporation of the solvent and distillation at 15 mm. gave cyclohexanone (4.7 g) and a caprolactam fraction (4.2 g) containing 93% by weight of caprolactam (by infra-red spectroscopy).

EXAMPLE 32

As in Example 31 but at the end of the reflux period the bulk of the methanol was evaporated at 15 mm Hg, the residue diluted with water, neutralised with acid and extracted with chloroform. Distillation gave cyclohexanone (4.1 g) and a caprolactam fraction (4.5 g), 87% pure by infra-red spectroscopy.

EXAMPLE 33

As in Example 31 but replacing methanol by ethanol. Heating time ½ hour. Distillation gave cyclohexanone (2.3g), a caprolactam fraction (3.7 g), a higher boiling fraction (2.4 g) and residue (0.7 g). The caprolactam fraction contained 70% by weight of caprolactam by infra-red spectroscopy.

EXAMPLE 34

Sodium (1.2 g) was dissolved in ethanol (50 cc) and peroxide (Ib) (10 g) in ethanol (40 cc) added. The resulting solution was refluxed for 4 hours, the bulk of the ethanol removed on the water pump and the residue treated as in Example 31. There were obtained cyclohexanone (2.5 g), caprolactam fraction (4.0 g) containing 76% by weight of caprolactam, a higher-boiling fraction (1.2 g) containing 10 – 15% caprolactam, and a residue (0.5 g).

EXAMPLE 35

Potassium (3.4 g) dissolved in methanol (30 cc) was treated with the peroxide (Ib) (10 g) in methanol (10 cc) and the mixture refluxed for 2 hours. The reaction mixture was treated as in Example 31 and gave cyclohexanone (3.6 g), a caprolactam fraction (3.8 g) containing 83% caprolactam, by weight, and a residue (0.5 g).

EXAMPLE 36

Lithium (0.8 g) dissolved in methanol (40 cc) and peroxide (Ib) (10 g) in methanol (10 cc were mixed and refluxed for 10½ hours. The reaction mixture was treated as in Example 1 and gave cyclohexanone (3.8 g), a caprolactam fraction, (2.7 g), containing 59% caprolactam by weight, a higher-boiling fraction (1.0 g) containing 30% caprolactam by weight, and residue (0.5 g).

EXAMPLE 37

Sodium (2 g) was dissolved in methanol (25 cc) and peroxide (Ib) (10 g) added, the mixture was refluxed for 1 hour. The reaction product was then diluted with water, and then extracted with chloroform without acidification to give cyclohexanone (2.9 g), a caprolactam fraction (4.8 g), containing 65% caprolactam by weight, a higher-boiling fraction (0.3 g), containing 37% caprolactam by weight and a residue (0.2 g).

EXAMPLE 38

Sodium n-butoxide (from 2 g of sodium) was dissolved in methanol (25 cc), and the peroxide (Ib) (10 g) in methanol (10 cc) added. The solution was heated under reflux for 1½ hours; the methanol was evaporated off under reduced pressure, water added to the residue and the solution extracted with chloroform. Distillation gave a fraction containing n-butanol and cyclohexanone (2.2 g of the ketone by estimation with hydroxylamine hydrochloride, a caprolactam fraction (5.1 g, containing 87% lactam by I.R. ) and a residue (0.3 g).

EXAMPLE 39

Sodium phenoxide (11.0 g) in methanol (30 cc) was mixed with peroxide (Ib) (10 g) in methanol (10 cc) and heated under reflux for 6¼ hours. The product was diluted with water, the solution extracted with chloroform and the extract distilled to give cyclohexanone (1.8 g), a caprolactam fraction (4.3 g, containing 70% lactam by I.R.) and residue (0.15 g).

The compounds described as "aroxides" may also be described as "aryloxides" but the slight difference in nomenclature does not affect the identity of the compounds concerned.

A process for the production of derivatives of alkane - α, ω-dioic acids having nitrogen bound to the ω-carbon atom comprises heating a compound of formula

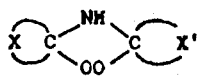 (F)

where X and X' are divalent aliphatic radicals which may be the same or different, at elevated temperatures.

In radicals X, X' the number of carbon atoms which are in the ring may for example vary from 4 to 11, i.e. there may be between 5 and 12 atoms in the ring. Examples of compounds of formula (F) are those compounds where X is a radical having 4 to 6 carbon atoms in the ring. Examples of such compounds are

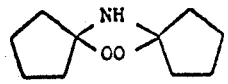

1,1'-peroxy dicyclopentylamino which is a white solid with a melting point of 22°–23°C.

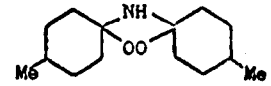

4,4'-dimethyl-1,1'-peroxydicyclohexylamine which is a white solid with melting point 119°–121°C.

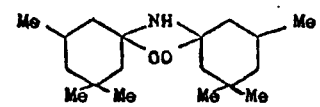

3,3,5,3',3',5' hexamethyl-1,1'-peroxydicyclohexylamino which boils at 115°C at a pressure of 2 mm. Hg. and

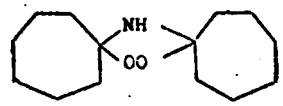

1,1'-peroxydicycloheptylamine which boils in the range 120°–130°C at a pressure of 0.8 mm. Hg.

In these alkane-dioic acid derivatives, the chain having the carboxy group or its derivative at either end will contain the same number of carbon atoms as the sum of the carbon atoms in the two rings, and this chain will a)

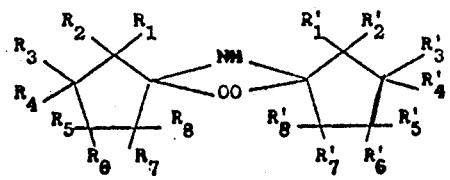

and b)

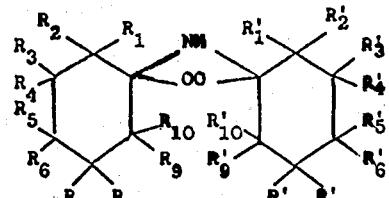 (E)

and c)

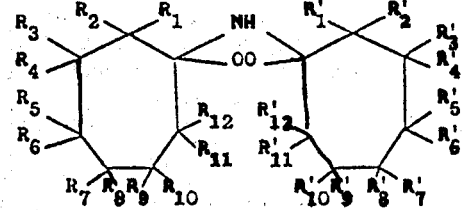

where R, R' are alkyl groups or hydrogen.

The preferred compounds are those in which R, R' is hydrogen or lower alkyl, e.g. methyl, ethyl, propyl.

Specific examples of compounds according to the present invention are:

carry substituents corresponding to the substituents on the two rings. Thus the nitrogen-containing alkane dioic acid derivatives prepared from a compound of formula (F) having an alkyl substituent in each ring will have two alkyl substituents on the chain containing the carboxy groups or the derivatives of the carboxyl groups e.g. —CONH₂, —CONHCO—, or —CN.

Examples of derivatives of alkane-α,ω-dioic acids containing nitrogen bound to the ω carbon atoms are

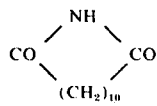 (IIc)

decan-1, 10-dicarbonimide

HOOC-(CH₂)₁₀-CN    (IIIc)

11-cyano-undecanoic acid

HOOC(CH₂)₁₀-CONH₂    (IVc)

11-carbamoyl-undecanoic acid and derivatives of these compounds in which the carbon chain carries alkyl substituents, e.g. 11-cyano-dimethyl-undecanoic acids.

The process may be carried out in the liquid or gas phase, but is preferably carried out in the gas phase as the liquid phase reaction tends to give a complex mixture of products of which only part are the desired derivatives of alkano-α,-ω-dioic acids. Examples of elevated temperatures to which the peroxyamine F is heated are those in the range 300°C to 600°C, and preferably from 400°C to 600°C. If the reaction is to be carried out in the gas phase it is preferred to use reduced pressures. Examples of suitable pressures are those of the order of 10 to 300 mm. Hg.

The vapour phase reaction may be carried out in any suitable manner, for example by feeding a solution of the peroxyamine into the top of a heated column, which may be packed with inert material e.g. glass balls and withdrawing the product containing the desired derivatives from the base. The pyrolysis may be carried out in an atmosphere of an inert gas, e.g. nitrogen. Any solvent which is inert to the conditions of the pyrolysis reaction may be used for dissolving the peroxide, e.g. ethanol, pyridine, β-picoline, benzene, chloroform, aqueous ethanol, cyclohexanone, tributylamine, ethylene glycol. The solution may be of any desired concentration for example 50–10% by weight peroxide in solvent. The peroxide may also be fed as a vapour without solvent, e.g. in a stream of inert gas.

The nature of the derivative of alkane-α,ω-dioic acid obtained by the process of the present invention will depend on the conditions used. If the reaction is carried out in the vapour phase the main products formed are derivatives of alkane-α,ω-dicarbonimide nitrile acids, and amide acids. As an example if 1,1'-peroxy-dicyclohexylamine is heated in the vapour phase at elevated temperature, the dicarbonimide is decane-1,10-dicarbonimide (IIc) the nitrile acid is 11-cyanoundocanoic acid (IIIc) and the acid-amide is 11-carbamoyl undocanoic acid (IVc). The skeletal structure of the derivatives produced will depend upon the nature and position of any substituents on the rings of the compound F fed to the reactor. The type of derivative produced will depend on the reaction conditions. High temperatures favour the formation of the nitrile-acid or its alkyl substituted derivatives. At a given temperature the proportion of nitrile-acid or its derivatives is increased by increasing the pressure at which the thermal decomposition is carried out, by decreasing the rate of feed to the heated column or by increasing the concentration of peroxide in the solvent, i.e. by increasing the contact time.

Examples of methods by which the derivative of alkane - α,ω-dioic acid may be separated from the crude product are distillation and recrystallization from solvents.

The thermal decomposition of compounds of formula F in addition to the derivatives of dioic acid compounds referred to above also yields lactams, cycloalkanones, which may be alkyl substituted depending upon the nature of any substituents in compound F. The number of carbon atoms in the lactam rings will be the same as that in the rings of the peroxyamine F from which they were derived and any substituents on the carbon atoms in the lactam ring will also correspond to those on the ring of the peroxyamine from which the lactam was derived. Thus a compound of formula

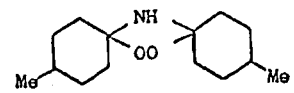

would give 4-methylcaprolactam and 4-methylcyclohexanone.

The process will be illustrated by the following examples.

EXAMPLE 40

A peroxide was prepared by reacting together 3-methylcyclohexanone, hydrogen peroxide, and ammonia. This peroxide was

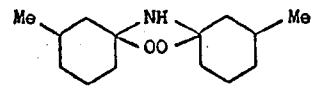

together with isomers in which the methyl group is also separated by a two carbon atoms in the chain from the carbon atom to which the peroxy group is attached. The peroxide (5 g.) was dissolved in ethanol (15 c.c.) and the solution dropped through a column (1.5 cm. internal diameter) containing 8 inches of glass beads and heated to 400°; the pyrolysis was carried out at 150 mm. pressure in a slight stream of nitrogen. Addition occupied ½ hr. The product was distilled to give 3-methylcyclohexanone (0.4 g.), a methylcaprolactam fraction (1.2 g.), and a fraction (2.6 g.), b.p. 190°–250°/14 mm., shown by I.R. and N.M.R. spectra to contain dimethyl-ω-cyanoundecanoic acid isomers as well as some lactam and amido-acid. The cyano acids were extracted with base, and had b.p. 230°–240°/14 mm.; acid equivalent, 238 (calc. 239).

EXAMPLE 41

A peroxide was prepared by reacting together 4-methylcyclohexanene, hydrogen peroxide, and ammonia. The resulting peroxide 4,4'-dimethyl-1,1'-peroxy dicyclohexylamino (5 g.) was dissolved in ethanol (60 c.c.) and the solution dropped through the heated column as in example 40 at 400°/150 mm. in 45 min. Part of the peroxide had not reacted, so that the product, after evaporation of the ethanol, was redissolved in benzene (20 c.c.) and the solution dropped through the same column in 1 hr. Distillation gave 4-methylcyclohexanone (0.6 g.), a 4-methylcaprolactam fraction (0.8 g.) and a fraction (1.8 g.), b.p. 180°-240°/14 mm., shown by I.R. spectroscopic examination to contain the expected dimethyl-ω-cyanoundocanoic acid as well as some amides and an unsaturated compound.

EXAMPLE 42

The peroxide (10 g.) from dihydroisophorene hydrogen peroxide and ammonia was dissolved in ethanol (15 c.c.) and the solution dropped through a heated column, as in example 40 at 500°/150 mm. during ¾ hr. Distillation of the product gave dihydroisophorene (1.7 g.), a trimethylcaprolactam fraction (2.4 g.), a fraction (1.6 g.), b.p. 180°-220°/15 mm. and a fraction (2.0 g.), b.p. 240°-246°/15 mm. containing nitrile acids.

EXAMPLE 43

The peroxide (10 g.) from cyclopentanono, hydrogen peroxide and ammonia was dissolved in ethanol (10 c.c.) and the solution dropped through a heated column as in example 40 at 500°C/150 mm. Hg during ¼ hr. Distillation of the product gave cyclopentanone (0.1 g.) valeric acid (0.3 g.), a cyano-nonanoic acid fraction (7.8 g.) residue (0.5 g.). The cyano acid had a melting point 50°-52°C on recrystallization.

Lactams may be polymerised to give useful products, e.g. caprolactam may be polymerised to give nylon-6.

A process for the production of lactams comprises reacting compounds of formula:

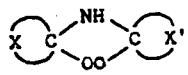

(F)

where X, X' are divalent aliphatic radicals which may be the same or different, with an alkali metal alkoxide or aryloxide or a mixture of an alkali metal hydroxide with an alkanol or a hydroxy-substituted aryl compound.

Compounds of formula (F) are produced as hereinbefore described. In radicals X, X' the number of carbon atoms which are in the ring may for example vary from 4 to 11, i.e. the total number of carbon atoms in the ring may be between 5 and 12. Examples of compounds of formula (F) are those compounds where X is a radical having 4 to 6 carbon atoms in the ring. Examples of such compounds are a)

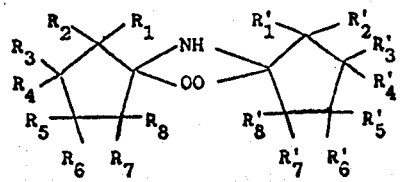

and b)

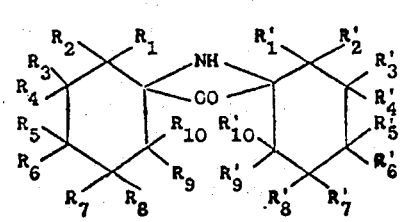

and c)

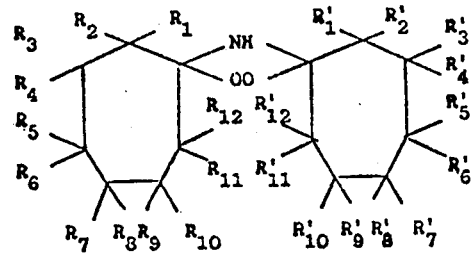

where R, R' are alkyl groups or hydrogen.

The preferred compounds are those in which R, R' is hydrogen or lower alkyl, e.g. methyl, ethyl, propyl.

Specific examples of compounds are:

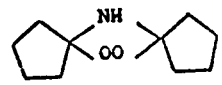

1,1'-peroxy dicyclopentylamine which is a white solid with a melting point of 22°-23°C.

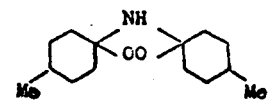

4,4'-dimethyl-1,1'-peroxydicyclohexylamino which is a white solid with melting point 119°-121°C.

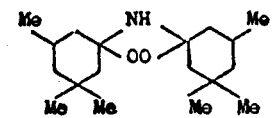

which boils at 124°-126° at a pressure of 0.4 mm. Hg.

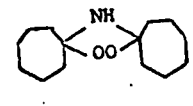

1,1'-peroxydicycloheptylamine which boils in the range 120°-130°C at a pressure of 0.8 mm. Hg.

These compounds may be made by the reaction of at least one cyclic ketone of formula

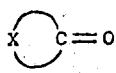

with hydrogen peroxide and ammonia, and can be considered, regardless of the method by which they are made, as derivatives of the cyclic ketones from which they could be formed.

The term "aryloxidos" as used herein means compounds formed by the replacement of hydrogen by a metal in a hydroxy group linked directly to an aromatic nucleus. An example of a suitable aroxide is sodium phenoxide

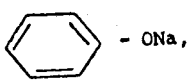

but other phenoxides including phenoxides with substituents other than hydroxy groups may be used. The preferred aroxides are those derived from the benzene nucleus. The term "hydroxyaryl compounds" as used in this specification means the compounds in which the hydroxy group is linked directly to an aromatic nucleus. Examples of suitable hydroxy-aryl compounds are those from which the "aryloxidos" referred to above may be derived.

The alkali metal alkoxide, aryloxide or hydroxide may be an alkoxide, aryloxide or hydroxide of any of the alkali metals, e.g. lithium, sodium or potassium. Sodium is particularly preferred.

Examples of suitable alkoxides are the lower alkoxides, e.g. ethoxide or methoxide, methoxides being preferred. Butoxides, in particular n-butoxides, are suitable and the use of n-butoxides is particularly advantageous, as they can be isolated from the reaction of n-butanol and alkali metal hydroxide It is not necessary however to isolate the alkoxide which may be formed in situ in the reaction mixture. If alkali metal hydroxides are combined with alkanols and hydroxy-aryl compounds with elimination of water, alkoxides or aryloxides will be produced, and the mixtures of alkali metal hydroxides with alkanols or hydroxy-aryl compounds will often contain alkoxides or aryloxides in equilibrium with the hydroxide. The presence of the water produced by the reaction of the alkanol or hydroxy aryl compound with the alkali metal hydroxide may however give rise to side-reactions which do not take place when the reaction is carried out using alkoxides or aryloxides prepared by methods which do not involve the production of water. Where mixtures of alkali metal hydroxide and alkanols are used examples of suitable alkanols are the lower alkanols, e.g. methanol, ethanol and butanol. The quantity of alkanol used is preferably in excess of 1 mole of alkanol per mole of alkali metal hydroxide. Preferably the quantity of alkanol is such that both the alkali metal hydroxide and peroxyamine are dissolved. The peroxide and hydroxide are preferably brought into contact in the absence of added water, e.g. in solution in a substantially anhydrous alkanol. It may be advantageous to carry out the reaction in the presence of a drying agent e.g. CaO, MgSO$_4$. The peroxyamine and the alkoxide or aryloxide may be reacted together in solution in a solvent such as aromatic hydrocarbons, e.g. benzene, phenols and/or alkanols, e.g. ethanol or methanol. Solvents of high dielectric constant lead to high rates of reaction although the yield of lactam may be reduced. The preferred solvents are alkanols and when an alkoxide is used, the alkanol is preferably the alkanol corresponding to the alkoxide, thus when using a methoxide the reactants are preferably dissolved in methanol and when using an ethoxide the reactants are preferably dissolved in ethanol. However, when using higher alkoxides and aryloxides the lower alkanols are the most suitable solvents. Thus, when using an n-butoxide, or a phenoxide, the most satisfactory results are obtained if the reaction with 1,1' peroxydicyclohexylamine or other peroxyamines is carried out in methanol.

Examples of suitable ratios of the number of moles of the alkali metal compound (whether alkoxide, aryloxide or hydroxide) to the number of moles of peroxyamine are 0.2 to 2. When the reaction is being carried out in solution the concentration of the reactants may vary within moderately wide limits.

The reaction can be carried out at moderately elevated temperatures. Examples of suitable temperatures are those in the range 40°–160°C, preferably temperatures of 50° to 100°C.

The duration of the reaction will vary with the temperature used, and the alkoxide and peroxyamine concentrations, the reaction being complete when no more peroxide can be detected in the reaction mixture. The presence of unreacted peroxide may be detected by reacting the reaction mixture with a known quantity of potassium iodide in acetic acid. Any peroxide present liberates iodine which can be estimated by titration with sodium thiosulphate. Examples of suitable times are those in the range 0.1 to 10 hours.

The reaction may be carried out at sub-atmospheric and super-atmospheric pressure as well as at atmospheric pressure. The reaction may be carried out under conditions such that the solvent is able to reflux when heated sufficiently and the pressure may then be such that the solvent used to dissolve the reactants refluxes at the reaction temperature, so helping to maintain the reaction temperature constant.

The lactam is recovered from the reaction mixture in any suitable manner for instance by diluting the reaction mixture with water followed by extraction of the mixture with a liquid which is immiscible with water and is a solvent for the lactam produced. Examples of suitable liquids are aromatic compounds, e.g. benzene, xylene, and chlorinated hydrocarbons especially the chlorinated lower aliphatic hydrocarbons, e.g. methylene chloride, chloroform, dichloroethane. Ethers, e.g. diethyl ether may also be used. Acid may optionally be added to the reaction mixture after addition of water. The quantity of acid is suitably such as to make the reaction mixture just acid to Congo red indicator. The solvent used to dissolve the reactants may be removed before the dilution with water if desired. The liquid used to extract the lactam is then distilled from the extract to leave the lactam and cyclic ketone which may be separated by e.g. distillation.

Where X and X' are the same, as when the peroxyamine F is formed from only one cyclic ketone, there will generally be two lactam isomers formed corresponding to introduction of nitrogen into the ring on either side of the carbon atom to which the peroxy group was attached, which will correspond to the carbon atom forming part of the carbonyl group in the ketone of which the peroxy amine F is a derivative. Thus a peroxyamine which is a derivative of 3-methylcyclohexanone is decomposed by the process of the present invention to give 3-methyl caprolactam and 5-methyl caprolactam

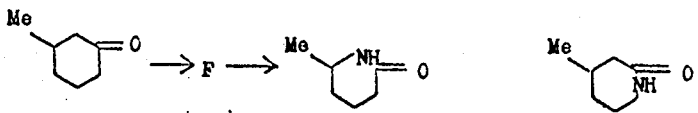

3-methyl hexanone   5-methyl caprolactam   3-methyl caprolactam

Where X and X' are different, different lactams will be formed from each ring and as it is possible for two isomers to be formed from a single ring it is possible to obtain a mixture of 4 lactams by reaction of a compound of formula F where X and X' are different.

The process will now be illustrated by the following examples.

EXAMPLE 44

The peroxide derived from 3-methylcyclohexanone, hydrogen peroxide and ammonia

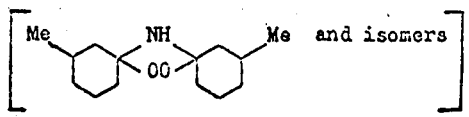

(10 g.) was added to a solution of sodium methoxide in methanol (2 g. sodium in 40 c.c. methanol), and the mixture heated under reflux for 2 hrs.; only a small amount of peroxide remained unreacted. The solution was cooled, diluted with water, neutralised with hydrochloric acid and extracted with chloroform. Distillation of the chloroform extract gave 3-methylcyclohexanone (4.7 g.), methylcaprolactam (4.1 g.), b.p. 145°–150°/15 mm., and residue (0.5g.). Examination of the methylcaprolactam fraction by N.M.R. spectroscopy showed it to be a mixture of 3- and 5-methylcaprolactam; on storage this fraction crystallised and several recrystallisations yielded the 3-methylcaprolactam, m.p. 97°–100°.

EXAMPLE 45

The peroxide derived from 4-methylcyclohexanone, hydrogen peroxide and ammonia

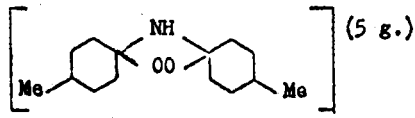

was added to a solution of sodium methoxide in methanol (1 g. of sodium in 20 cc. methanol) and the mixture heated under reflux for 2 hr. when very little peroxide remained unreacted. The product was worked up as in Example 44 to give, on distillation, 4-methylcyclohexanone (2.2 g.), 4-methylcaprolactam (2.2 g.), b.p. 145°–150°/15mm., and residue (0.3 g.). The structure of the lactam was confirmed by I.R. and N.M.R. spectra.

EXAMPLE 46

The peroxide derived from dihydroisophorene, ammonia and hydrogen peroxide

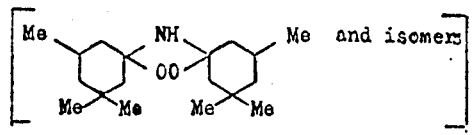

(75 g.) was added to a solution of sodium methoxide in methanol (1.5 g. of sodium in 30 cc. methanol) and the mixture heated under reflux for 2 hr. when very little peroxide remained unreacted. The product was worked up as in Example 44 to give, on distillation, dihydroisophorene (4.1 g.), trimethylcaprolactam (3.1 g.), and residue (0.1 g.). The structure of the lactam was confirmed by I.R. and N.M.R. spectra; the N.M.R. spectrum showed that both

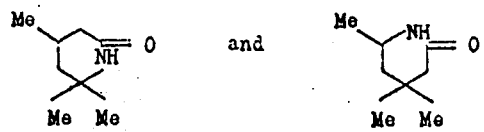

were present, the latter being the major component.

EXAMPLE 47

The peroxide derived from cyclopentanone, ammonia and hydrogen peroxide (1,1' amino dicyclopentyl peroxide) (10 g.) was heated to reflux with sodium (2 g.) in methanol (40 cc.). After reflux for ¼ hr the product was worked up as in Example 44 and valerolactam obtained.

Valerolactam was also obtained when the experiment was repeated using 5 g. of the peroxide, 0.65 g. of sodium and a reflux time of 2½ hours.

Accordingly the present invention comprises the class of compounds having the structural unit

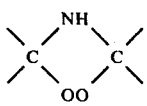   (1)

A wide range of atoms and groups may be attached to the free valencies in the structure (I)

Examples of groups which may be attached to the free valencies in structure (I) are hydrogen, alkyl and aryl groups. One, or both, of the carbon atoms in structure (I) may form part of a ring or rings into which they are bonded by their free valencies. Examples of suitable rings are those containing from 5 to 7 carbon atoms or more in the ring, and this ring may be joined to other rings.

It is found that compounds in which one or more of the free valencies are linked to hydrogen atoms may tend to be unstable and decompose. If therefore it is desired to store a compound of structure (I) for any length of time it should preferably not contain any hydrogen atoms bound to the free valencies.

Where neither of the carbon atoms in structure (I) forms part of a ring, it is preferred that at least one alkyl group be bonded to each carbon atom in the structure (I) the Examples of such compounds are the compounds containing the structural unit

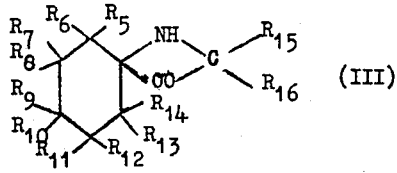

where $R_5$ to $R_{14}$ are hydrogen or alkyl groups, $R_{15}$ is alkyl and $R_{16}$ is hydrogen, alkyl and aryl. The alkyl group $R_{15}$, and $R_{16}$ when an alkyl group, are preferably lower alkyl groups for example those having less than 10, preferably less than 5 carbon atoms.

$R_5$ to $R_{14}$ may be hydrogen or alkyl and examples of suitable alkyl groups are the lower alkyl groups e.g. those having 1 to 5 carbon atoms in particular methyl, ethyl and propyl groups although longer alkyl chains may be also be used. Examples of compounds of formula (III) are those in which at least one of $R_5$ to $R_{14}$ is an alkyl group, in particular at least one of $R_7$ to $R_{12}$ is an alkyl group while $R_5$, $R_6$, $R_{13}$ and $R_{14}$ are hydrogen. An example of a particularly suitable pattern of substituents is that in which $R_7$ and $R_8$ are both methyl, while one of $R_{11}$ and $R_{12}$ is methyl the remaining $R_5$ to $R_{14}$ being hydrogen.

Both carbon atoms in the structural unit (I) may form part of rings into which they are bonded by the free valencies shown in the structure (I) and examples of such compounds are those of formula

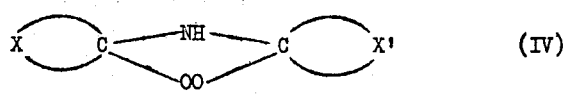

where X,X' are divalent aliphatic radicals which may be the same or different.

In radicals X, X' the number of carbon atoms which are in the ring may for example vary from 4 to 11, i.e. the total number of carbon atoms in the ring may be between 5 and 12. Carbon atoms may be the only atoms in the ring. Examples of compounds of formula (IV) are those compounds where X is a radical having 4 to 6 carbon atoms in the ring. Examples of such compounds are:

(a)
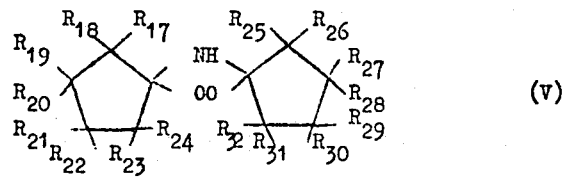

(b)
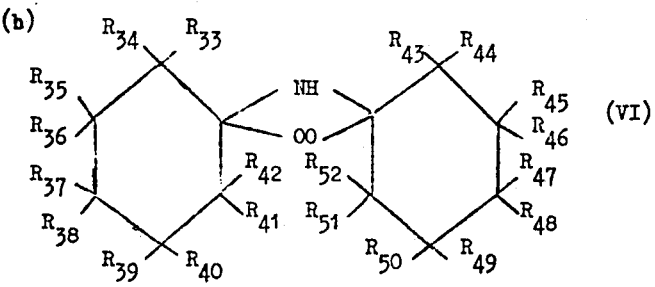

and (c)
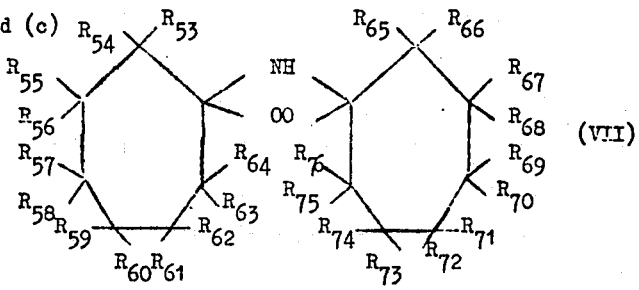

where $R_{17}$ to $R_{76}$ are alkyl groups or hydrogen.

The preferred compounds are those in which $R_{17}$ to $R_{76}$ is hydrogen or lower alkyl, e.g. methyl, ethyl, propyl although the compounds may have longer chains.

Specific examples of compounds according to the present invention are:

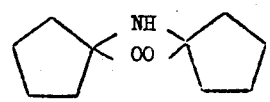

1,1'-peroxydicyclopentylamine which is a white solid with a melting point of 22° – 23°C.

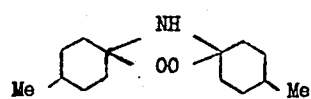

4,4'-dimethyl-1,1'-peroxydicyclohexylamine which is a white solid with melting point 119° – 121°C.

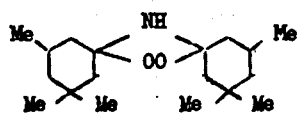

3,3,3',3',5,5'-hexamethyl-1,1'-peroxydicyclohexylamine which boils at 124° – 126°C at a pressure of 0.4 mm.Hg.

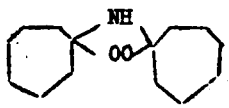

1,1'-peroxydicycloheptylamine which boils in the range 120° – 130°C at a pressure of 0.8 mm.Hg.

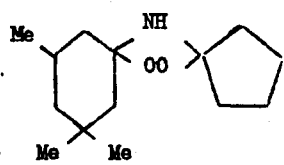

1,1'-peroxy-3,3,5-trimethylcyclohexyl cyclopentylamine which boils at 92° – 96°C at 0.3 mm.Hg.

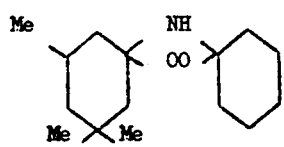

1,1'-peroxy-3,3,5-trimethylcyclohexyl cyclohexylamine

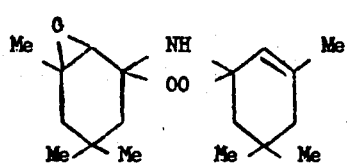

b.p. 136° – 141°C at 0.3 mm.Hg.

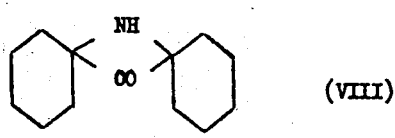

1,1'-peroxydicyclohexylamine which is a white solid insoluble in water but soluble in ethanol, which melts at 40° – 41.5°C and distills at 94° – 97°C at a pressure of 0.4 mm.Hg. and at 138° – 140°C at a pressure of 12 mm.Hg.

The present invention also includes a process for making compounds having the essential skeletal structure (I) by reacting together at least one compound having the essential skeletal structure:

with hydrogen peroxide and ammonia.

The free valencies of the carbon atom in the structure (IX) may be satisfied by any group which will be inert under the reaction conditions i.e. will not enter into reaction with ammonia or hydrogen peroxide.

The carbonyl compound may be acyclic or cyclic. Where the carbonyl compound is acyclic examples of suitable groups which may be bound to the free valencies are hydrogen and alkyl preferably lower alkyl. It is preferred that at least one alkyl group is bound to a free valency of the carbon atom of structure (IX) the other group being hydrogen or alkyl, to give compounds of formula $$R_{77}R_{78}CO \qquad (X)$$

where $R_{77}$ is alkyl and $R_{78}$ is hydrogen or alkyl. Preferably alkyl groups are bound to both free valencies. Specific examples of carbonyl compounds which may be used are acetone, ethyl methyl ketone, and n-butyraldehyde.

The compounds formed by reaction of a compound of formula (X) with hydrogen peroxide and ammonia are those of formula (II)

In place of acyclic carbonyl compounds, at least one compound of formula

where X is a divalent aliphatic radical may be used. Carbon atoms may be the only atoms in the ring. The cyclic ketone may be for example a ketone with between 5 and 12 carbon atoms in the ring, would then have 4 – 11 carbon atoms forming part of the ring.

Examples of suitable ketones are those of formulae

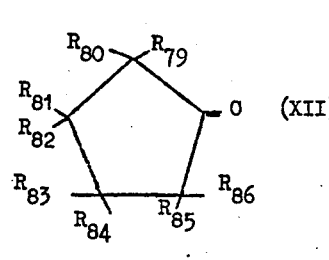

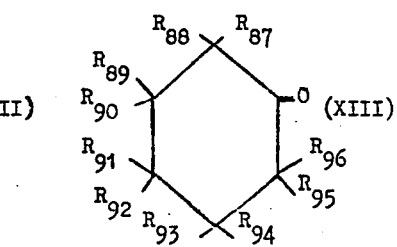

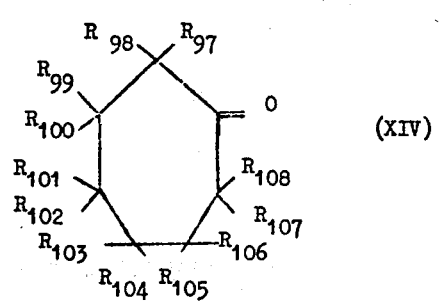

where $R_{79}$ to $R_{108}$ are alkyl groups or hydrogen.

The preferred compounds are those where $R_{79}$ to $R_{108}$ are hydrogen or lower alkyl e.g. methyl, ethyl, propyl, but compounds with longer alkyl chains can also be used. Examples of compounds of the above formulae which may be used are those in which not more than one alkyl group is joined to each carbon atom in the ring. Compounds in which two alkyl groups are joined to a single carbon atom may be used, however. When the ring is a 6 carbon atom ring, then any gem-dialkyl groups are preferably substituted in positions 3,4 or 5 on the ring.

Examples of ketones which may be used are cyclopentanone, 2-methylcyclohexanone, 3-methylcyclohexanone, 4-methylcyclohexanone, 3,3,5-trimethylcyclohexanone (dihydroisophorone), and cycloheptanone.

The compounds produced by reaction of a compound of formula (XI) with hydrogen peroxide and ammonia are those of formula (IV). Where only one compound of formula (XI) is used, and the radical X is inert under the reaction conditions the radicals X and X' in the compound of formula (IV) will be the same although the compound of formula (IV) may exist in a number of different stereoisomers.

It is possible that formation of compounds having the structural unit (I) from carbonyl compounds having the structure (IX) by reaction with ammonia and hydrogen peroxide proceeds by way of compounds containing the structural unit

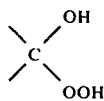
(XV)

and

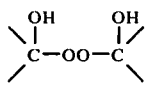
(XVI)

and where compounds of formula (XV) and (XVI) exist they may be reacted with ammonia to give compounds containing the structural unit (I). Thus the formation of compounds containing the structural unit (IV) by reaction of compounds of formula (XI), hydrogen peroxide and ammonia may proceed by way of compounds of formula

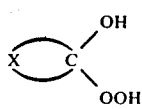
(XVII)

and

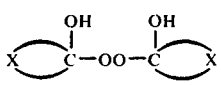
(XVIII)

where X is a divalent aliphatic radical, and where peroxides of the above formula can be formed e.g. by oxidation of cyclic alcohols with molecular oxygen or by reaction of cyclic ketones with hydrogen peroxide, these peroxides may be reacted with ammonia to give compounds of formula (IV)

Thus 1,1'-dihydroxydicyclohexyl peroxide

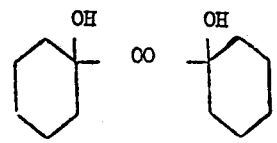

can be reacted with ammonia to give 1,1'-peroxydicyclohexylamine.

In the same way of formation of compounds of formula (II) from compounds of formula (X), hydrogen peroxide and ammonia may proceed by way of compounds of formula

(XIX)

or

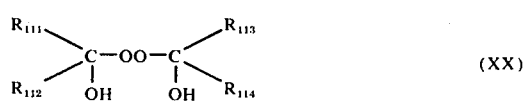
(XX)

where $R_{109}, R_{111}$ and $R_{113}$ have the same meaning as $R_{77}$ in formula (X) while $R_{110}, R_{112}$ and $R_{114}$ have the same meaning as $R_{78}$ in formula (X) and where these exist they may be reacted with ammonia to give compounds of formula (II).

It is possible that the formation of the compounds of formula (IV) from compounds of formula (XI), hydrogen peroxide and ammonia may proceed by way of an intermediate of formula

(XXI)

which then reacts further. Where compounds of formula (XXI) can be isolated they may be reacted with compounds (IX) to give compounds of formula (I). Thus compounds containing the structural unit (I) may be prepared by reacting a compound of formula

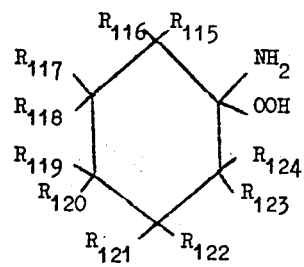
(XXII)

with a compound containing the structural unit

  (IX)

R₁₁₅ to R₁₂₄ have the same meaning as R₅ to R₁₄ in structure (III) and the remarks made concerning R₅ to R₁₄ in connection with structure (III) apply also to R₁₁₅ to R₁₂₄ in the compound of formula (XXII). Before proceeding with the discussion of the reaction of (XXII) and (IX) it will be necessary to discuss the preparation of (XXII). Compounds of structure (XXII) may be prepared by reacting together a cyclic ketone of formula

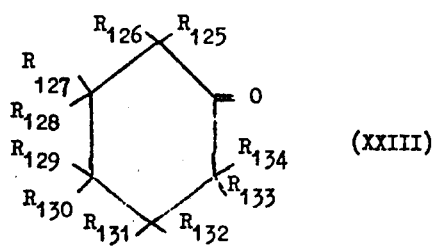  (XXIII)

with ammonia and hydrogen peroxide where R₁₂₅ to R₁₃₄ have the same meaning as R₅ to R₁₄ in formula (III) and the remarks made concerning R₅ to R₁₄ in connection with (III) apply also to R₁₂₅ to R₁₃₄ in (XXIII). A particularly preferred compound of formula (XXIII) is 3,3,5-trimethylcyclohexanone, as the compound of formula (XXII) namely 1-amino-3,3,5-trimethylcyclohexyl hydroperoxide is readily isolated from the reaction mixture before further reaction takes place.

A novel compound of formula (XXII) which may be produced by the process described above is 1-amino-3,3,5-trimethylcyclohexyl hydroperoxide. This compound whose structure was established by nuclear magnetic resonance and infra-red spectroscopy, and by elemental analysis is unstable if kept at temperatures much above 0°C and melts with decomposition at 67° – 67.5°C. The compound may be made by the process of the present invention using dihydroisophorone as the cyclic ketone

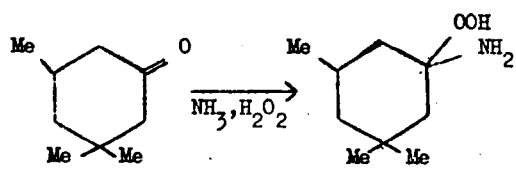

Another novel compound which may be made by the process of the present invention is 1-amino-4-methylcyclohexyl hydroperoxide which may be made by the process of the present invention using 4-methylcyclohexanone as starting material.

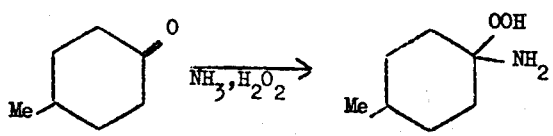

Other novel compounds of formula (XXII) are 1-aminocyclohexylperoxide

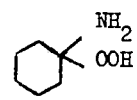

which has m.p. 57° – 58°C (rapid heating), 47°C with decomposition (slow Heating), and 1-aminocyclododecyl hydroperoxide which has m.p. of 72° – 73°C.

Having discussed the formation of the compounds of formula (XXII) I will return to the reaction of these compounds with compounds of formula (IX). The comments made concerning the groups which may be on the free valencies of the compound containing the structural unit (IX) in connection with the preparation of compounds containing the structural unit (I) apply also to the reaction of (XXII) and (IX). Thus compounds of formula (X) may be used, to give products of formula (II) while compounds of formula (XI) give products of formula (IV)

Examples of specific carbonyl compounds which may be used are formaldehyde, acetaldehyde, n-butyraldehyde, acetone, ethyl methyl ketone, diethylketone, acetophenone, cyclopentanone, cycloheptanone, and 3,3,5-trimethylcyclohexanone.

All the reactions described above can be carried out with a catalyst, although catalysts can be used, by bringing the reactants into contact. This may be done by mixing the reactants in the liquid phase. Where the reactants are all liquids or gases as may often be the case when carbonyl compounds of structure (IX), hydrogen peroxide and ammonia are being reacted together, simple mixing of the reactants may be sufficient. Where one of the reactants is a solid it may be dissolved in a solvent, which should preferably be miscible with the other constituents of the reaction mixture. Thus when reacting carbonyl compounds with hydrogen peroxide and ammonia the solvent used should be miscible, preferably completely, with hydrogen peroxide and water. Even if the reactants are all liquids or gases it may be desirable to add a solvent to ensure adequate contact between the reactants. Thus when reacting carbonyl compounds, hydrogen peroxide and ammonia together it may be desirable to add a liquid which is a solvent for the carbonyl compound and is miscible preferably completely with hydrogen peroxide and water. It may often be convenient to use a solvent in which the reactants are soluble and the desired reaction product insoluble so that the reaction product can be separated from the reaction mixture by filtration. This may be particularly useful when dealing with the less stable products, as the need to carry out distillations or solvent extractions which can cause considerable losses of product is thereby avoided. Examples of solvents which may be used are methanol, ethanol, light petroleum, ether, dioxan, dimethylformamide.

When bringing reactants into contact to carry out the reaction it is not essential that all the reactants should be entirely in the liquid phase and it may be desirable to mix the reactants together in the presence of a solvent for one of the reactants and the reaction product.

Where hydrogen peroxide is a reactant it will generally be in the form of an aqueous solution. The strength of this solution may vary between moderately wide limits. Examples of suitable hydrogen peroxide solutions are those containing between 5–100% by weight of the total solution of hydrogen peroxide. Thus commercially available solutions containing about 28–30% by weight of hydrogen peroxide are satisfactory. The reaction mixture may contain a hydrogen peroxide stabiliser e.g. sodium ethylene diamine tetraacetate (BDTA).

The concentration of hydrogen peroxide in the reaction mixture in which it is used will depend not only on the strength of the hydrogen peroxide solution added but on the quantities of other reactants and solvents present. The quantity of hydrogen peroxide in the reaction mixture may vary over a wide range. Examples of suitable concentrations of hydrogen peroxide in the reaction mixture are those in the range 5–40% by weight, particularly suitable concentrations being those in the range 10–20% by weight.

In the reaction of carbonyl compound (IX) with hydrogen peroxide and ammonia the molar ratio of ketone and hydrogen peroxide reacted together may vary over a moderately wide range for example between 4:1 and 0.5:1 but when preparing compounds having the structural unit (I) it is preferred to use at least two moles of ketone for one mole of hydrogen peroxide the stoichiometric ratio being 2:1. When it is desired to prepare compounds of formula (XXII) it is preferred to use a molar ratio of ketone to hydrogen peroxide of about 1:1, this being the stoichiometric ratio for the reaction.

Where ammonia is a reactant it may be fed into the reaction mixture in the form of a gas or as a solution in for example water. The concentration of the ammonia solution may vary over moderately wide limits and 0.880 ammonia i.e. an aqueous solution having a relative density of 0.880, is suitable. If desired the reaction may be started with the ammonia added to the other reactants as a solution and may be continued by passing gaseous ammonia into the reaction mixture. Where ammonia is a reactant it is preferred to use a slight excess over the stoichiometric quantity but the quantity of ammonia is not critical.

The temperatures at which the reactions described above may be carried out will depend upon the thermal stability of the reactants and products as the use of temperatures sufficiently high to decompose the reactants and products must be avoided.

When preparing compounds of structure (I) in which the free valencies of both carbon atoms do not bond the carbon atoms into a ring e.g. when preparing compounds of formulae: (II) or (III). Examples of temperatures which may be used are temperatures in the range −20°C to +20°C, in particular −10°C to +10°C. When reacting compounds of formula (XI) with hydrogen peroxide and ammonia or compounds of formula (XVII) or (XVIII) with ammonia it may be possible to use a somewhat wider range of temperatures, for example temperatures in the range −20°C to +60°C, preferably those in the range 0°C to 50°C. Temperatures of about 40°C are often particularly suitable. In the preparation of compounds of formula (XXII) and in the reaction of those compounds with compounds (IX) it is preferred to use temperatures in the range −20°C to +20°C, for example temperatures in the range −10°C to +10°C in particular temperatures below 0°C. The duration of the reaction when preparing compounds containing the structural unit (I) will depend upon the temperature and the particular reactants used and may vary over a wide range. The reaction may be complete in 2 to 3 hours but longer times may sometimes be desirable.

When preparing amino-hydroperoxides of formula (XXII) it may be necessary to control the reaction time carefully to prevent the compound (XXII), reacting further. The optimum time for this reaction can be determined by the man skilled in the art and may for example range from ½ to 7 hours. The pressure in the reactions described above may vary over a moderately wide range, atmospheric pressure or pressures close to atmospheric pressure generally being most convenient. When carrying out reaction in which ammonia is a reactant pressures below atmospheric pressure will cause a reduction in the ammonia concentration in the reaction system which may lead to reduced yields and it may be desirable to use pressures above atmospheric pressure to obtain a high concentration of ammonia.

The reactions described above can be carried out batchwise or continuously.

The peroxide (I) and (XXII) may be recovered in any suitable manner or may be used, without recovery, in further reactions. Where the reaction is carried out in aqueous solution the peroxide of formula (I) will generally separate out as a solid or in a liquid layer from the aqueous solution. Where the peroxide (I) is to be reacted further, this product rich in peroxide (I) can be separated from the reaction mixture and used without further purification. Alternatively the peroxide (I) may be extracted from the reaction using a suitable organic solvent e.g. chloroform, ether, light petroleum, benzene, or ethyl acetate. The peroxide (I) may then be separated from the extract by distillation, if necessary under reduced pressure, provided that the distillation temperature is not so high as to decompose the peroxide. Alternatively, it may be possible to precipitate the peroxide from the extract by addition of water. It may also be possible to obtain the solid crystalline peroxide directly by filtration from the reaction mixture.

The 1-amino-hydroperoxides (XXII) will often precipitate from the reaction mixture and can be separated by filtration from the reactants. Where other products are obtained which are insoluble in the reaction mixture it may often be possible to dissolve these other products with hydrophobic solvents e.g. light petroleum.

It should be noted that the compounds according to the present invention are not restricted to those made from carbonyl compounds (IX) carrying groups which are inert under the reaction conditions. The groups bonded to the free valencies shown in structure (I) may well differ from those found in the compounds from which the compound of structure (I) is prepared. Thus when ammonia and hydrogen peroxide are reacted together with a carbonyl compound which contains groups which react with ammonia and/or hydrogen peroxide it may often still be possible to obtain compounds containing the structural unit (I) but the groups bonded to the free valencies in the structure (I) will not necessarily then be the same as those bonded to the carbonyl group in the starting material.

The invention will now be illustrated by the following Examples. The perchloric acid equivalents of substances given in the examples were determined by titrating an anhydrous N/10 solution of perchloric acid in acetic acid with a solution in acetic acid of a weighed sample of the substance whose equivalent is being determined. The peroxide or active oxygen equivalents of substances given in the examples were determined by adding a saturated solution of potassium iodide (containing a quantity of potassium iodide in excess of that required to react with all the peroxide groups in the substance under investigation), to acetic acid to which a small quantity of sodium bicarbonate is added to generate carbon dioxide. A weighed sample of the substance under investigation is then added, the mixture heated on a boiling water bath for 5 minutes, and then cooled. A little water is then added and the mixture titrated with N/10 sodium thiosulphate solution.

EXAMPLE 48

Acetone (58 g.), 30% hydrogen peroxide (70 c.c.) and the sodium salt of E.D.T.A. (1.0 g.) were mixed and saturated with gaseous ammonia at about 0°C., and the solution stored overnight at 0°C. The solution was extracted with ether and the ethereal extract dried and evaporated. Distillation of the residue gave a fraction (21.1 g.), b.p. 55°C/12 m.m.Hg., which on redistillation gave a product b.p. 40° – 42°C at 12 m.m.Hg. This product on analysis was shown on the basis of elemental analysis, nuclear magnetic resonance, and infra-red spectroscopy to be 2,2'-peroxy-diprop-2-ylamine

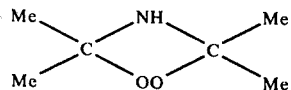

The peroxide equivalent was 135 and the perchloric acid equivalent was 147. The elemental analysis gave C, 55.05%; H, 10.1%; N, 10.2%.

EXAMPLE 2

Ethyl methyl ketone (72 g.), 30% hydrogen peroxide (70 c.c.), ammonium acetate (8 g.) and sodium salt of E.D.T.A. (1. - g.) were mixed and treated with gaseous ammonia as in Example 1. The solution was stored at 0°C overnight and then extracted with ether. Distillation of the ethereal extract gave a fraction (46.7g.), b.p. 66° – 68°C at 12 m.m.Hg. pressure. The peroxide equivalent was 157, the perchloric acid equivalent was 161 and the elemental analysis was C,59.4%; H,10.85%; N,8.4%.

This was identified as 2,2'-peroxy-dibut-2-ylamine

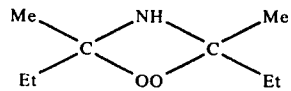

EXAMPLE 3

A mixture of n-butyraldehyde (72 g.), 30% hydrogen peroxide (70 c.c.), methanol (45 c.c.), ammonium acetate (8 g.) and sodium salt of E.D.T.A. (1 g.) was cooled to about 0°C and saturated with gaseous ammonia. The solution was stored at 0°C overnight and extracted with ether. The ethereal extract was evaporated to leave a residue (74.5 g.) having a peroxide equivalent of 171. A small portion of this residue was distilled to give a fraction b.p. 50°C at 0.1 m.m.Hg., with peroxide equivalent of 165 and a perchloric acid equivalent of 188, and elemental analysis C,60.5%; H,10.95% and N,8.9%.

This product was identified as 1,1'-peroxy-dibut-1-ylamine

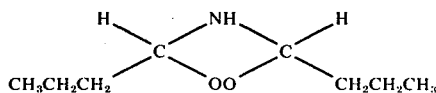

EXAMPLE 51

A mixture of isophorone (41.4 g.), 30% hydrogen peroxide (45.2 c.c.), methanol (350 c.c.), 0.880 ammonia (80 c.c.), and sodium salt of E.D.T.A. (1.0 g.) was cooled to temperatures at or below 0°C and saturated with gaseous ammonia, then stored at 0°C for several days. A solid (0.8 g.) was filtered off, rinsed with cold ethanol and refiltered, to give material with m.p. 74° – 81°C, perchloric acid equivalent 179. Elemental analysis gave C, 56.2%; H, 9.2%; N, 7.1%. Spectroscopic evidence showed this to be the 1-amino-1-hydroperoxide of epoxyisophorone

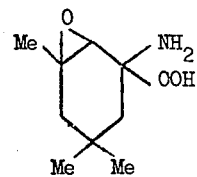

The filtrate was extracted with ether and the ethereal extract evaporated and distilled to give a fraction (27.7 g.) b.p. 54°C at 0.3 mm. Hg; consisting mainly of isophorone epoxide with some isophorone, and a fraction (3.4 g.) b.p. 136° – 141°C at 0.3 mm. Hg, with perchloric acid equivalent of 340 and active oxygen equivalent of 199. Elemental analysis gave C, 69.4%, H, 9.2%, N, 5.3%.

This peroxide

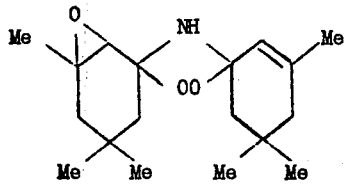

was of the type according to the present invention and this example illustrates the production of compounds according to the present invention from carbonyl compounds in which the groups bound to the carbonyl group are not inert.

EXAMPLE 52

1-Amino-3,3,5-trimethylcyclohexyl hydroperoxide (34.6 g.) was added with stirring to acetaldehyde (12 g.) in petrol (light petroleum spirit (b.p. 40° – 60°C))(60 c.c.) with the temperature kept at below 0°C. When the peroxide had dissolved, the aqueous layer was separated, and the organic phase treated with concentrated sulphuric acid (6 drops) and magnesium sulphate and left at room temperature. The solution was then filtered, washed with water, dried, and distilled. In addition to dihydro-isophorone a product (32.0 g.) was obtained which boiled at 70° – 78°C at 0.5 mm. Hg. pressure, and had a peroxide equivalent of 221. Elemental analysis gave C, 66.3%; H, 10.6%; H, 7.0%. This was identified as:

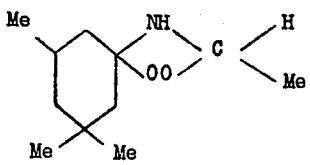

EXAMPLE 53

1-Amino-3,3,5-trimethylcyclohexyl hydroperoxide (17.3 g; 78% pure) was added with stirring to acetaldehyde (12 g.) in light petroleum (b.p. 40° – 60°C) (50 c.c.) with cooling to below 0°C. When the hydroperoxide had dissolved, the organic layer was separated, treated with solid magnesium sulphate and stored at 0°C overnight. The solution was then filtered, washed and distilled as in Example 52 and gave, in addition to dihydroisophorone, the same product (13.0 g.) as Example 52.

EXAMPLE 54

The process of Example 52 was repeated but using 17.3 g. of 78% pure 1-amino-3,3,5-trimethylcyclohexyl hydroperoxide, 30 c.c. of light petroleum and 3 drops of sulpuric acid. The reaction mixture was allowed to stand at 0°C for 4 hours and then worked up as in Example 52 to give the same peroxide product as in Example 52 (15.4 g.).

This product on redistillation had a b.p. of 68° – 74°C at 0.5 mm.Hg. pressure. On analysis the redistilled product gave C, 66.3%; H,10.6%; N, 7.0%. The calculated values were C, 66.3%; H, 10.55%; N, 7.0%.

EXAMPLE 55

Butyraldehyde (14.4 g.) was mixed with petrol (b.p. 40° – 60°) (50 c.c.) and to the stirred solution at below 0°C was added 1-amino-3,3,5-trimethylcyclohexyl hydroperoxide (17.3 g.; 89% pure). The peroxide dissolved within a few minutes. To the solution were added magnesium sulphate and concentrated sulphuric acid (6 drops) and the mixture stored at 0°C overnight. The solution was filtered, the filtrate washed with water, dried and distilled to give unreacted butyraldehyde, dihydroisophorone and a product (11.1 g.), b.p. 85° – 110°C/1.0 mm. with a peroxide equivalent of 231, and a perchloric equivalent of 233. The elemental analysis gave C, 68.6%; H, 11.05%; N, 6.6%. The product was identified as:

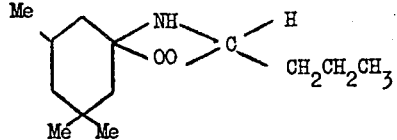

EXAMPLE 56

Butyraldehyde (28.8 g.) in petrol (100 c.c.) was cooled to below 0°C and with stirring treated with 1-amino-1-hydroperoxy-3,3,5-trimethylcyclohexane (33 g.; 93% pure). When the solid had dissolved the aqueous phase was removed and the petrol solution dried with magnesium sulphate overnight at 0°C. The working up as in Example 55 gave butyraldehyde, dihydroisophorone and the same peroxide (33.0 g.) b.p. 96° – 98°C/ 0.6 mm, as in Example 55.

EXAMPLE 57

Formaldehyde (17.2 g. of 35% aqueous solution) was stirred in ether (50 c.c.), together with sodium bicarbonate (2 g.) at below 0°C (and 1-amino-3,3,5-trimethylcyclohexyl hydroperoxide (16.5 g.; 96% pure) added. When the solid had dissolved the aqueous layer was removed and magnesium sulphate added to the ethereal solution, which was stored at 0°C for 2 hours. The solution was filtered and the filtrate evaporated at 15 mm.; the residue was then heated to 54°C at 0.6 mm. Hg. pressure and the fresh residue (9.0 g.), with a peroxide equivalent of 312, was shown, by mass spectrometry, to contain the peroxide

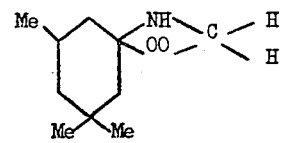

together with higher molecular weight material.

EXAMPLE 58

Acetone (11.6 g.) in ethanol (50 c.c.) was stirred at below 0°C and 1-amino-3,3,5-trimethylcyclohexyl hydroperoxide (17.3 g; 80% pure) added. After stirring for ca. 1 hour the solid had dissolved. To the solution was added magnesium sulphate and it was stored at 0°C overnight. Filtration and distillation gave acetone and dihydroisophorone (probably containing some symmetrical amino-peroxide

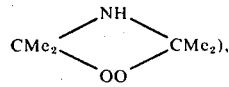

and a product (2.2 g.), b.p. 75° – 78°C/1.0 mm, had a peroxide equivalent 239.4 and gave N, 6.3% an elemental analysis.

This was identified as the peroxide

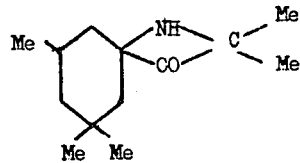

Redistillation of the peroxide gave a sample of the peroxide with a peroxide equivalent of 222, perchloric acid equivalent 235.

EXAMPLE 59

To a stirred mixture of ethyl methyl ketone (57.6 g.) and ethanol (200 cc.), containing ammonium acetate (6.4 g.) and kept at or below 0°C was added 1-amino-3,3,5-trimethylcyclohexyl hydroperoxide (69.2 g;

pure). After the solid had dissolved the solution was stored at 0°C overnight. The product was worked up as in the previous Examples to give, on distillation, unreacted ethyl methyl ketone, a fraction (59.4 g.), b.p. 40° – 50°C/0.4 mm.Hg., having a peroxide equivalent of 303 and shown by mass spectroscopy to be a mixture of dihydroisophorone and the symmetrical peroxide

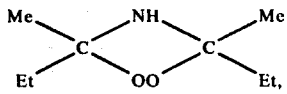

and a fraction (22 g.), b.p. 74° – 78°C/0.4 mm., with a peroxide equivalent of 231 and perchloric acid equivalent of 227. The elemental analysis gave C, 69.0%; H, 11.2%; N, 5.8% which was identified as being the peroxide

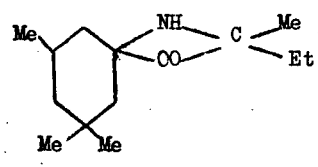

EXAMPLE 60

To a stirred solution of acetophenone (24.3 g.) in ethanol (50 c.c.) containing ammonium acetate (1.6 g.) and kept at or below 0°C, was added 1-amino-3,3,5-trimethylcyclohexyl hydroperoxide (17.3 g.; pure). The solution was kept at 0°C overnight and then worked up as in the previous Examples to give unreacted acetophenone and dihydroisophorone, and a fraction (4.8 g.), b.p. 126° – 130°C/0.5 mm.Hg. with a peroxide equivalent of 407, shown by mass spectroscopy to contain the peroxide

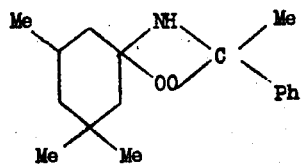

together with some of the symmetrical peroxide

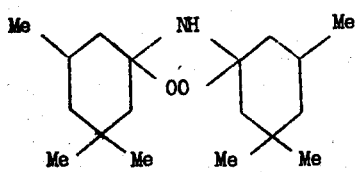

EXAMPLE 16

To a stirred mixture of cyclopentanone (33.8 g.) and ethanol (100 c.c.) containing ammonium acetate (3.2 g.) and kept at or below 0°C, was added 1-amino-3,3,5-trimethylcyclohexyl hydroperoxide (44.6 g., 68% pure). After storing at 0°C overnight the reaction mixture was worked up as in the previous Examples to give unreacted cyclopentanone and dihydroisophorone together with a fraction (20.0 g.) b.p. 82° – 86°/0.5 mm.Hg. This last fraction was redistilled to give: material b.p. 74° – 76°C/0.3 mm.Hg., peroxide equivalent 202, shown by mass spectroscopy to be a mixture of the peroxide

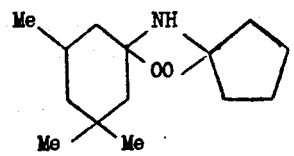

with the symmetrical peroxide

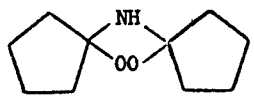

and material b.p. 92° – 96°C/0.3 mm, Hg. peroxide equivalent 232, shown to be the unsymmetrical component of the mixture referred to above. On analysis the elements found were: C, 69.2%; H, 10.4%; N, 6.1%.

EXAMPLE 62

To a stirred mixture of cycloheptanone (73.2 g.) and ethanol (200 cc.), containing ammonium acetate (6.4 g.) and kept at or below 0°C was added 1-amino-3,3,5-trimethylcyclohexyl hydroperoxide (69.2 g.; 76% pure). After the solid had dissolved (5 hours) the solution was stored at 0°C overnight and the product worked up as in the previous Examples. There were obtained unreacted cycloheptanone, and dihydroisophorone, and fractions (57.5 g.) b.p. 124° – 130°C/0.3 mm.Hg., peroxide equivalent 283, perchloric acid equivalent 278 shown by mass spectroscopy to contain the peroxide

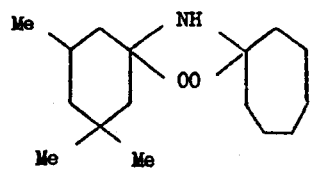

The elemental analysis gave C, 70.9%; H, 10.9%; N, 5.05% in agreement with the formula.

EXAMPLE 63

To a stirred mixture of dihydroisophorone (28 g.) and ethanol (50 cc.), containing ammonium acetate (1.6 g.) kept at or below 0°C was added 1-ammino-3,3,5-trimethylcyclohexyl hydroperoxide (17.3 g.; pure). The mixture was stored at 0°C for 4 days and then worked up as in the preceding Examples to give dihydroisophorone and a fraction (12.0 g.) b.p. 126° – 128°C at 0.4 mm.Hg; peroxide equivalent 322. The elemental analysis gave C, 73.3%; H, 11.1% N, 5.0%.

The product was identified as 1,1'-peroxy-3,3,5,3',-3',5'-hexamethyl-dicyclohexylamine

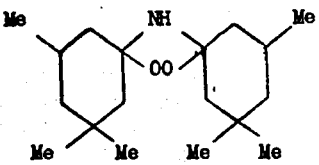

EXAMPLE 64

To a stirred mixture of cyclohexane (19.6 g.) and ethanol (50 c.c.), kept at or below 0°C, was added 1-amino-3,3,5-trimethylcyclohexyl hydroperoxide (17.3 g., 78% pure); solution was complete in ca. 10 min. To the solution was added conc. sulphuric acid (3 drops) and magnesium sulphate and the mixture was stored at 0°C for 3 days. The solid was filtered off, the filtrate washed with water, dried and distilled, to give cyclohexanone, dihydroisophorone and a fraction (11.5 g.), b.p. 90° – 100°C at 0.02 mm. Hg., peroxide equivalent 179. By mass spectroscopy the product was shown to contain the unsymmetrical peroxide 1,1'-amino-3,3,5-trimethylcyclohexylamine.

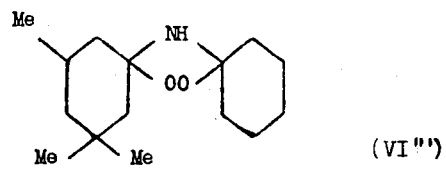

(VI''')

and the symmetrical peroxide 1,1'-peroxydicyclohexylamine in the ratio 1:9.

EXAMPLE 65

To a stirred solution of cyclohexanone (19.6 g.) in ethanol (50 cc), containing ammonium acetate (1.6 g.) and kept at or below 0°C was added 1-amino-3,3,5-trimethylcyclohexyl hydroperoxide (17.3 g.; 78% pure). The solid dissolved in 5 – 10 min., then to the solution was added magnesium sulphate and the mixture stored at 0°C overnight. Working up as in the previous Examples led to isolation of a peroxide fraction (13.1 g.) b.p. 98° – 104°C/0.3 mm., with ratio of (VII''') of 1:9:8.

EXAMPLE 66

The reaction of Example 65 was repeated with the stirring carried out at −30°C, and overnight storage at −10°C. There was obtained peroxide (10.5 g.) having a ratio of (VI''') of 1:8.

EXAMPLE 67

To a stirred solution of cyclohexanone (19.6 g.) in dioxan (30 c.c.) kept at or below 0°C was added 1-amino-3,3,5-trimethylcyclohexanone (17.3 g.; 78% pure). After the solid had dissolved magnesium sulphate was added and the solution stored overnight at 0°C. Working up as in the previous Examples gave peroxide (4.5 g.) with a ratio of (VI''') to (VIII) of 1:12:1.

EXAMPLE 68

The process of Example 67 was repeated, but replacing the dioxan by dimethylformamide. There was obtained peroxide (10.5 g.) with a ratio of (VI''') to (VIII) of 1:8:6.

EXAMPLE 69

2-Methylcyclohexanone (51 g.), methanol (60 cc.), 0.880 ammonia (35 c.c.), 30% hydrogen peroxide (35 cc.) and EDTA (0.5 g.) were mixed together at room temperature and the solution saturated with gaseous ammonia. After standing together for one week, the product was extracted with ether, the extract dried with magnesium sulphate, the solvent evaporated, 2-methyl-cyclohexanone (21.3 g.) removed at 0.3 mm.Hg., and the residue treated with petrol. Some petrol-insoluble material, m.p. 77° – 79°C, was separated, and petrol-soluble portion evaporated and residue distilled to give the required peroxide (7.9 g.), b.p. 107°C/0.4 mm.Hg., and residue (0.6 g.). Redistillation of the peroxide gave material (b.p. 97°–100°C/0.07 mm.Hg.) having an active oxygen equivalent of 247, and a perchloric acid equivalent of 244. Elemental analysis gave C, 70.4%, H, 10.3%; N, 8.4%. The structure of the peroxide was confirmed by I.R. and N.M.R. spectroscopy as 1,1'-peroxy-2,2'-dimethyl-dicyclohexylamine

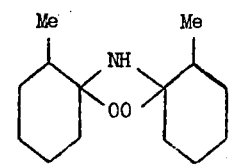

EXAMPLE 70

3-Methylcyclohexanone (50 g.), methanol (60 cc.), 0.880 ammonia (35 cc.), 30% hydrogen peroxide (35 cc.) and EDTA (0.5 g.) were mixed together at room temperature and saturated with gaseous ammonia. After standing for one week the product was extracted with ether. Distillation of the extract yielded 3-methyl-cyclohexanone and a product (27.1 g.), b.p. 105°C/0.2 mm.Hg., and a residue (1.0 g.). The product was identified as 1,1'-peroxy-3,3'-dimethyldicyclohexylamine

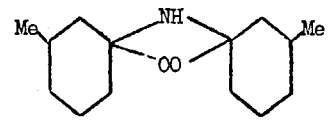

The peroxide equivalent was 235 and the perchloric acid equivalent was 256. The structure was confirmed by I.R. and N.M.R. spectroscopy.

EXAMPLE 71

4-Methylcyclohexanone (50 g.), methanol (120 cc.), 0.880 ammonia (135 cc.), 30% hydrogen peroxide (35 cc.), and EDTA (0.5 g.) were mixed at room temperature and the solution saturated with gaseous ammonia. The mixture was stored for one week during which time a solid product had separated. The product was extracted with light petrol (b.p. 40° – 60°C) to give some insoluble material (6.8 g.), m.p. 79° – 80°C (dec.), the 1-amino-4-methylcyclohexyl hydroperoxide; peroxide equivalent (active oxygen), 147.5; perchloric acid equivalent 165. The petrol-soluble material was obtained as solid (26.4 g.) m.p. 119° – 121°C; active oxygen equivalent 224; perchloric acid equivalent, 235. The elemental analysis gave C, 70.1%; H, 10.5%; N, 6.0%. The I.R. and N.M.R. spectra were in agreement with this product being the desired 4,4'-dimethyl-1,1'-peroxy-dicyclohexylamine. The non-crystalline material (9.0 g.) contained unreacted 4-methyl-cyclohexanone together with further peroxide.

EXAMPLE 72

Dihydroisophorone (128 g.), 0.880 ammonia (240 cc.), 30% hydrogen peroxide (120 cc.), and EDTA (sodium salt) (2 g.) were mixed and methanol (450 cc.) added in sufficient quantity to give a homogeneous solution. The mixture was stirred at ca. 0°C in a stream of ammonia and after a short time solid began to appear. When the solution became thick with solid it was filtered and the filtrate retreated with ammonia to yield further solid.

Distillation of the mother liquors from the reaction product from which the solid had been separated, yielded a small amount of the symmetrical peroxide 1,1'-peroxy-3,3,5,3',3',5'-hexamethyl dicyclohexylamine

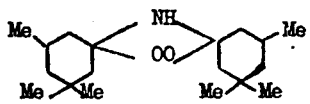

b.p. 115°C at 0.2 mm Hg. Elemental analysis gave C, 73.3%; H, 11.1%; N, 5.0%. The structure was confirmed by I.R. and mass spectrometry.

EXAMPLE 73

Cyclopentanone (77.5 g.), 0.880 ammonia (50 cc.), water (20 cc.), methanol (45 cc.), E.D.T.A. (sodium salt) (1.0 g.) and ammonium acetate (8.0 g.) were stirred together, and 30% hydrogen peroxide (70 cc.) added with cooling. After storing the mixture for two days at 0°C. the solution was extracted with ether. The ether extract, on distillation, yielded a low-boiling fraction (56 g.) b.p. 71°/0.1 mm.Hg. This product had a peroxide equivalent of 172, and perchloric acid equivalent of 195. Elemental analysis gave C, 4.7%; H, 8.9%; N, 7.6%. It solidified on storage and, when crystallized from cold petrol, had m.p. 22° – 23°C. This product was identified as 1,1'-peroxy-dicyclopentylamine.

EXAMPLE 74

Cycloheptanone (50 g.), methanol (60 cc.), 0.880 ammonia (35 cc.), 30% hydrogen peroxide (35 cc.) and E.D.T.A. (0.5 g.) were mixed at room temperature, saturated with gaseous ammonia and stored for one week. Extraction with ether, followed by distillation of the extract yielded cycloheptanone (44 g.), and a product (5.5 g.), b.p. 120° – 130°C/0.8 mm.Hg., which had peroxide equivalent 331 and perchloric equivalent 306. This was identified as

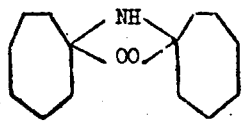

1,1'-peroxy-dicycloheptylamine and a residue (1.6 g.).

EXAMPLE 75

Cyclohexanone (90 g.) ammonia (50 cc.), water (20 cc.), methanol (45 cc.) and E.D.T.A. (1 g.) were stirred together and 30% hydrogen peroxide (70 cc.) gradually added with the reaction temperature kept at or below −35°C. The mixture was stored at room temperature overnight, the product extract with ether, and the extract evaporated and the residue distilled to give cyclohexanone (22 g.) and a product which was identified as 1,1'-peroxy-dicyclohexylamine (64.4 g.), and leave a residue (2.0 g.). The peroxide distils at 94° – 97°C/0.4 mm. Hg., 138°–140°C/12 mm, Hg and has a melting point of 40° – 41.5°C.

EXAMPLE 76

The same conditions were used as in Example 28 except that after the period of storage the bottom oily layer was separated, dissolved in ethanol, and the ethanolic solution added, with stirring, to water (2 litres). The 1,1'-peroxy-dicyclohexylamine separated as solid and filtered off. The yield of slightly wet product was 82 g., redistillation giving 72.6 g. of pure peroxide.

EXAMPLE 77

Cyclohexanone (90 g.), 0.880 ammonia (32 cc.), water (20 cc.), methanol (45 cc.) and E.D.T.A. (0.2 g.) were stirred together and 30% hydrogen peroxide (70 cc.) gradually added with the reaction temperature kept at or below 35°C. The mixture was stored at room temperature overnight, the oily layer separated, diluted with an equal volume of methanol and the methanolic solution added, with stirring, to cold water (2 litres). Solid was filtered off and on distillation gave the peroxide 1,1'-peroxy-dicyclohexylamine (71.5 g.).

EXAMPLE 78

Cyclohexanone (90 g.), 0.880 ammonia (50 cc.), water (20 cc.), methanol (45 cc.) and E.D.T.A. (1.0 g.) were stirred together, and 30% peroxide (70 cc.), added, with the reaction temperature kept at or below 30°C. The temperature was kept at 35°C for 4 hours and gaseous ammonia slowly passed into the solution. The mixture was stored overnight at room temperature; the peroxide crystallised out from the solution on addition of water and was filtered off. Distillation gave cyclohexanone (3.5 g.) and 1,1'-peroxy-dicyclohexylamine (77.8 g.). The aqueous phase was extracted with ether and provided cyclohexanone (4.8 g.) and no peroxide.

EXAMPLE 79

1,1'-Dihydroxydicyclohexyl peroxide (26.5 g.), 0.880 ammonia (12.5 cc.), water (35 cc.), methanol (12 cc.) and E.D.T.A. (0.2 g.) were stirred together until the solid peroxide had dissolved and the mixture left at room temperature overnight. The product was extracted with ether and the ethered extract on distillation, gave cyclohexanone (<1 g.) and 1,1'-peroxydicyclohexylamine (17.6 g.).

The 1,1'-peroxydicyclohexylamine may also be made by reacting the autoxidate of cyclohexanol i.e. the product of oxidation of cyclohexanol with molecular oxygen, with ammonia.

EXAMPLE 80

A mixture of dihydroisophorone (44.9 g.; 0.31 mole), 0.880 ammonia (110 cc.), ethanol (150 cc.), and E.D.T.A. (sodium salt) (0.5 g.) was cooled and ca. 30% hydrogen peroxide (40 cc.; 0.375 mole) added. The stirred mixture was kept at below 0°C and ammonia gas passed in. After 6 hours the solid produced was filtered off and the filtrate cooled and retreated with ammonia. Two further crops of solid were obtained. The solid had perchloric acid equivalent of 181 and peroxide equivalent of 164 and elemental analysis gave C, 65.2%; H, 10.9%, N, 7.8%, was washed with water, cold alcohol, then petrol, and dried in vacuo: yield, 33.4 g. (0.19 mole). The product was identified as 1-amino-3,3,5-trimethylcyclohexyl hydroperoxide.

The filtrate washings were found to contain 0.15 mole unreacted hydrogen peroxide and 0.115 mole dihydroisophorone.

EXAMPLE 81

Dihydroisophorone (44.9 g.; 0.31 mole), 0.880 ammonia (60 cc.), methanol (150 cc.), and E.D.T.A. (sodium salt) (0.5 g.) were mixed and cooled; ca 30% hydrogen peroxide (40 cc.; 0.375 mole) was added, and the stirred, cooled mixture treated with ammonia as above.

There were obtained 1-amino-3,3,5-trimethylcyclohexyl hydroperoxide (48.9 g.; 0.275 mole), dihydroisophorone (4.3 g.; 0.31 mole), and there was present in the filtrate and washings 0.1 mole unreacted hydrogen peroxide.

EXAMPLE 82

4-Methylcyclohexanone (50 g.), methanol (120 cc.), 0.880 ammonia (135 cc.), 30% hydrogen peroxide (35 cc.) and E.D.T.A. (0.5 g.) were mixed at room temperature (ca. 20°C) and the solution saturated with gaseous ammonia. The mixture was stored for one week, during which time a solid product separated. The product was extracted with light petrol (b.p. 40° – 60°C). Insoluble material (6.8 g.) remained after the extraction. This material had m.p. 79° – 80°C (dec.) peroxide equivalent 147.5 perchloric acid equivalent 165 and was identified as 1-amino-4-methylcyclohexyl hydroperoxide.

EXAMPLE 83

Cyclododecanone (60.6 g.) was mixed with ethanol (450 cc.), 86% hydrogen peroxide (13.4 g.), 0.880 ammonia solution (20 cc.) ammonium acetate (3 g.) and E.D.T.A. (sodium salt; 1 g.), the solution saturated with gaseous ammonia and stored at ca. 0°C for 3 days. The solid aminohydroperoxide (57.6 g) was filtered off. A portion recrystallised from benzene had m.p. 72° – 73°C, a peroxide equivalent of 210, and perchloric acid equivalent of 215 (calco. 215). The I.R. and N.M.R. spectra were in agreement with the proposed structure, and it had an elementary analysis of C, 66.3; H, 11.5; N, 6.1%. Calc. for $C_{12}H_{25}NO_2$: C, 66.9; H, 11.6; N, 6.5%.

EXAMPLE 84

30% Hydrogen peroxide (70 cc.) was added rapidly to a stirred solution of cyclohexanone (49 g.) and E.D.-T.A. (sodium salt) (0.5 g.) in methanol (30 cc.) and 0.880 ammonia (55 cc.). The temperature rose to ca. 30°C, but rapid cooling reduced this to 0° – 15°C; storage for 1 hour at below 0°C caused crystallisation. The product was filtered off, washed well with ice-cold water, then petrol, and dried on a porous plate; this product (57 g.), and m.p. 57° – 58°C (rapid heating), 47°C (slow heating) with decomposition) and had a peroxide equivalent of 140 and perchloric acid equivalent of 135 (calc 131). Found: C, 55.1; H, 9.85; N, 10.9; calc for $C_6H_{13}NO_2$: C, 55.0; H, 9.95; N, 10.7%.

I claim:
1. A process for the production of a compound of the formula

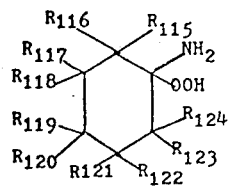

wherein at least one of $R_{117}$ to $R_{122}$ is the same substituent selected from the group consisting of methyl, ethyl and propyl and the rest are each hydrogen; and $R_{115}$, $R_{116}$, $R_{123}$ and $R_{124}$ are each hydrogen; which comprises reacting a compound of the formula

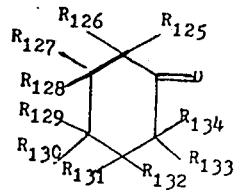

wherein at least one of $R_{127}$ to $R_{132}$ is the same substituent selected from the group consisting of methyl, ethyl and propyl and the rest are each hydrogen; and $R_{125}$, $R_{126}$, $R_{133}$ and $R_{134}$ are each hydrogen; with hydrogen peroxide and ammonia.

2. A process according to claim 1 wherein $R_{117}$ and $R_{118}$ are each methyl; one of $R_{121}$ and $R_{122}$ is methyl and the other is hydrogen; $R_{115}$, $R_{116}$, $R_{119}$, $R_{120}$, $R_{123}$ and $R_{124}$ are each hydrogen; $R_{127}$ and $R_{128}$ are each methyl; one of $R_{131}$ and $R_{132}$ is methyl and the other is hydrogen; and $R_{125}$, $R_{126}$, $R_{129}$, $R_{130}$, $R_{133}$ and $R_{134}$ are each hydrogen.

3. A process according to claim 1 wherein the reactants are mixed together in the presence of a solvent in which the compound of the formula

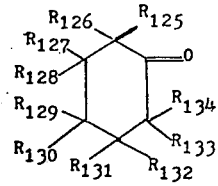

is soluble and which is miscible with water and hydrogen peroxide.

4. A process according to claim 1 wherein the mole ratio of the compound of the formula

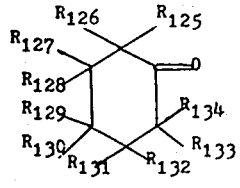

to hydrogen peroxide is about 1:1.

5. A process according to claim 4 wherein the reaction is carried out at a temperature of from −20°C to +20°C.

6. A process according to claim 4 wherein the reaction is carried out at the temperature of from −10°C to +10°C.

7. A process according to claim 4 wherein the compound of the formula

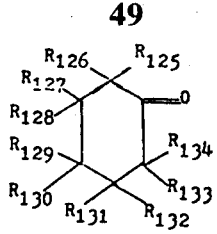
is 3,3,5-trimethylcyclohexanone or cyclohexanone.
8. The compound 1-amino-3,3,5-trimethylcyclohexyl hydroperoxide.
9. The compound 1-amino-cyclododecyl hydroperoxide.
10. The compound 1-amino-1-hydroperoxide of epoxyisophorone.
* * * * *